(12) United States Patent
Batchelder et al.

(10) Patent No.: US 8,658,250 B2
(45) Date of Patent: Feb. 25, 2014

(54) ENCODED CONSUMABLE MATERIALS AND SENSOR ASSEMBLIES FOR USE IN ADDITIVE MANUFACTURING SYSTEMS

(75) Inventors: J. Samuel Batchelder, Somers, NY (US); Michael D. Bosveld, Bloomington, MN (US)

(73) Assignee: Stratasys, Inc., Eden Prairie, MN (US)

( * ) Notice: Subject to any disclaimer, the term of this patent is extended or adjusted under 35 U.S.C. 154(b) by 334 days.

(21) Appl. No.: 13/075,667

(22) Filed: Mar. 30, 2011

(65) Prior Publication Data

US 2011/0233804 A1 Sep. 29, 2011

Related U.S. Application Data

(63) Continuation-in-part of application No. 12/949,898, filed on Nov. 19, 2010, which is a continuation-in-part of application No. 12/622,042, filed on Nov. 19, 2009.

(60) Provisional application No. 61/262,771, filed on Nov. 19, 2009.

(51) Int. Cl.
*B05D 1/26* (2006.01)

(52) U.S. Cl.
USPC .......................................... 427/256; 264/40.4

(58) Field of Classification Search
USPC .................. 427/256; 264/40.4; 428/364, 375
See application file for complete search history.

(56) References Cited

U.S. PATENT DOCUMENTS

| | | | |
|---|---|---|---|
| 3,017,060 A | 1/1962 | Miller | |
| 4,137,446 A | 1/1979 | Blanpain et al. | |
| 4,749,347 A | 6/1988 | Valavaara | |
| 4,797,313 A | 1/1989 | Stolk et al. | |
| 5,121,329 A | 6/1992 | Crump | |
| 5,169,081 A | 12/1992 | Goedderz | |
| 5,303,141 A | 4/1994 | Batchelder et al. | |
| 5,312,224 A | 5/1994 | Batchelder et al. | |
| 5,340,433 A | 8/1994 | Crump | |
| 5,342,687 A | 8/1994 | Iwai et al. | |
| 5,461,239 A | 10/1995 | Atherton | |
| 5,503,785 A | 4/1996 | Crump et al. | |
| 5,738,817 A | 4/1998 | Danforth et al. | |
| 5,764,521 A | 6/1998 | Batchelder et al. | |
| 5,866,058 A | 2/1999 | Batchelder et al. | |

(Continued)

FOREIGN PATENT DOCUMENTS

| | | |
|---|---|---|
| DE | 19909170 A1 | 9/2000 |
| EP | 0684092 | 11/1995 |

(Continued)

OTHER PUBLICATIONS

International Search Report and Written Opinion dated May 12, 2011, from International Application No. PCT/US2010/057398, filed Nov. 19, 2010.

*Primary Examiner* — Michael Cleveland
*Assistant Examiner* — Alex A Rolland
(74) *Attorney, Agent, or Firm* — Brian R. Morrison; Westman, Champlin & Koehler, P.A.

(57) ABSTRACT

A consumable material and sensor assembly for use in an additive manufacturing system, the consumable material comprising an exterior surface having encoded markings that are configured to be read by the sensor assembly, where the consumable material is configured to be consumed in the additive manufacturing system to build at least a portion of a three-dimensional model.

20 Claims, 17 Drawing Sheets

(56) References Cited

U.S. PATENT DOCUMENTS

| | | |
|---|---|---|
| 5,939,008 A | 8/1999 | Comb et al. |
| 5,968,561 A | 10/1999 | Batchelder et al. |
| 6,004,124 A | 12/1999 | Swanson et al. |
| 6,022,207 A | 2/2000 | Dahlin et al. |
| 6,054,077 A | 4/2000 | Comb et al. |
| 6,067,480 A | 5/2000 | Stuffle et al. |
| 6,070,107 A | 5/2000 | Lombardi et al. |
| 6,085,957 A | 7/2000 | Zinniel et al. |
| 6,129,872 A | 10/2000 | Jang |
| 6,228,923 B1 | 5/2001 | Lombardi et al. |
| 6,257,517 B1 | 7/2001 | Babish et al. |
| 6,429,889 B1 | 8/2002 | Murokh |
| 6,547,995 B1 | 4/2003 | Comb |
| 6,645,412 B2 | 11/2003 | Priedeman, Jr. |
| 6,650,815 B2 | 11/2003 | Hawtof et al. |
| 6,685,866 B2 | 2/2004 | Swanson et al. |
| 6,722,872 B1 | 4/2004 | Swanson et al. |
| 6,730,252 B1 | 5/2004 | Teoh et al. |
| 6,749,414 B1 | 6/2004 | Hanson et al. |
| 6,790,403 B1 | 9/2004 | Priedeman, Jr. et al. |
| 6,814,907 B1 | 11/2004 | Comb |
| 6,866,807 B2 | 3/2005 | Comb et al. |
| 6,869,559 B2 | 3/2005 | Hopkins |
| 6,923,634 B2 | 8/2005 | Swanson et al. |
| 6,998,087 B1 | 2/2006 | Hanson et al. |
| 7,032,814 B2 | 4/2006 | Blankenship |
| 7,122,246 B2 | 10/2006 | Comb et al. |
| 7,172,715 B2 | 2/2007 | Swanson et al. |
| 7,363,686 B2 | 4/2008 | Fukuyasu et al. |
| 7,996,101 B2 | 8/2011 | Menchik et al. |
| 2005/0279819 A1* | 12/2005 | Stava .......................... 235/375 |
| 2007/0003656 A1 | 1/2007 | LaBosiee et al. |
| 2007/0228590 A1 | 10/2007 | LaBossiere et al. |
| 2008/0213419 A1 | 9/2008 | Skubic et al. |
| 2009/0035405 A1 | 2/2009 | Leavitt |
| 2009/0263582 A1 | 10/2009 | Batchelder |
| 2009/0273122 A1 | 11/2009 | Batchelder |
| 2009/0274540 A1 | 11/2009 | Batchelder |

FOREIGN PATENT DOCUMENTS

| | | |
|---|---|---|
| EP | 1065620 A2 | 1/2001 |
| GB | 816016 | 7/1959 |
| WO | 9737810 A1 | 10/1997 |
| WO | 2008/075101 | 6/2008 |

* cited by examiner

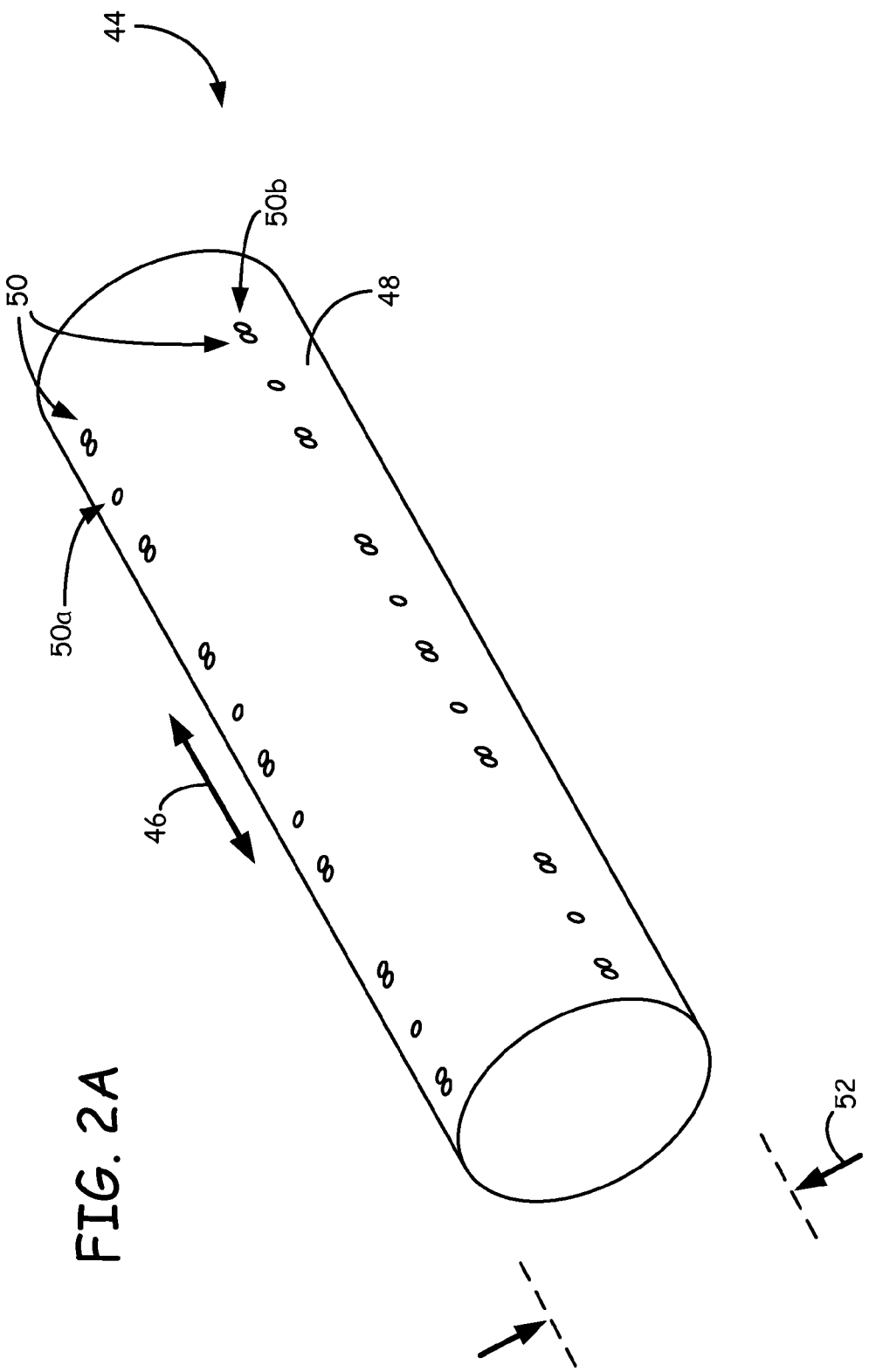

ENCODED CONSUMABLE MATERIALS AND SENSOR ASSEMBLIES FOR USE IN ADDITIVE MANUFACTURING SYSTEMS

CROSS-REFERENCE TO RELATED APPLICATION(S)

This application is a continuation-in-part of U.S. patent application Ser. No. 12/949,898, filed on Nov. 19, 2010; and entitled "Encoded Consumable Materials And Sensor Assemblies For Use In Additive Manufacturing Systems", the disclosure of which is incorporated by reference in its entirety.

U.S. patent application Ser. No. 12/949,898 is a continuation-in-part of U.S. patent application Ser. No. 12/622,042, filed on Nov. 19, 2009, and entitled "Consumable Materials Having Encoded Markings For Use With Direct Digital Manufacturing Systems"; and of U.S. Provisional Patent Application No. 61/262,771, filed on Nov. 19, 2009, and entitled "Optical Sensor Assembly For Use With Consumable Materials Having Encoded Markings"; the disclosures of which are incorporated by reference in their entireties.

BACKGROUND

The present disclosure relates to direct digital or additive manufacturing systems for building three-dimensional (3D) models. In particular, the present disclosure relates to consumable materials, such as modeling and support materials, for use in additive manufacturing systems, such as extrusion-based additive manufacturing systems, and to sensors for use with the consumable materials.

An extrusion-based, direct digital or additive manufacturing system (e.g., fused deposition modeling systems developed by Stratasys, Inc., Eden Prairie, Minn.) is used to build a 3D model from a digital representation of the 3D model in a layer-by-layer manner by extruding a flowable consumable modeling material. The modeling material is extruded through an extrusion tip carried by an extrusion head, and is deposited as a sequence of roads on a substrate in an x-y plane. The extruded modeling material fuses to previously deposited modeling material, and solidifies upon a drop in temperature. The position of the extrusion head relative to the substrate is then incremented along a z-axis (perpendicular to the x-y plane), and the process is then repeated to form a 3D model resembling the digital representation.

Movement of the extrusion head with respect to the substrate is performed under computer control, in accordance with build data that represents the 3D model. The build data is obtained by initially slicing the digital representation of the 3D model into multiple horizontally sliced layers. Then, for each sliced layer, the host computer generates a build path for depositing roads of modeling material to form the 3D model.

In fabricating 3D models by depositing layers of a modeling material, supporting layers or structures are typically built underneath overhanging portions or in cavities of objects under construction, which are not supported by the modeling material itself. A support structure may be built utilizing the same deposition techniques by which the modeling material is deposited. The host computer generates additional geometry acting as a support structure for the overhanging or free-space segments of the 3D model being formed. Consumable support material is then deposited from a second nozzle pursuant to the generated geometry during the build process. The support material adheres to the modeling material during fabrication, and is removable from the completed 3D model when the build process is complete.

SUMMARY

An aspect of the present disclosure is directed to a marked consumable material for use in an additive manufacturing system. The marked consumable material includes an exterior surface and encoded markings at the exterior surface, where at least a portion of the encoded markings denote volume increments along the marked consumable material. The encoded markings are configured to be read by at least one optical sensor configured to be operated by the additive manufacturing system. The marked consumable material is also configured to be consumed in the additive manufacturing system to build at least a portion of a three-dimensional model.

Another aspect of the present disclosure is directed to an additive manufacturing system that includes a bay configured to receive a supply of a marked consumable material. The marked consumable material includes an exterior surface and encoded markings at the exterior surface, where the encoded markings extend along at least a portion of a longitudinal length of the marked filament at locations that denote volume increments of the marked consumable material along the longitudinal length. The additive manufacturing system also includes a deposition head configured to receive and dispense the marked consumable material to build a three-dimensional model using a layer-based, additive technique on a platform. The additive manufacturing system further includes a sensor configured to detect the encoded markings of the marked consumable material as the marked consumable material is fed to the deposition head, and a controller in signal communication with the deposition head and the sensor, where the controller is configured to adjust a dispensing rate of the marked consumable material onto the platform in response to the detected encoded markings by the sensor.

Another aspect of the present disclosure is directed to a method for building a three-dimensional model with an additive manufacturing system. The method includes loading a spool to the additive manufacturing system, where the spool has a marked consumable material comprising an exterior surface having encoded markings, and where at least a portion of the encoded markings denote volume increments of the marked consumable material along a longitudinal length of the marked consumable material. The method also includes feeding the marked consumable material to a deposition head of the additive manufacturing system, and reading information from the encoded markings of the fed marked consumable material with an optical sensor assembly. The method further includes transmitting the read information to a controller of the additive manufacturing system, and adjusting at least one property of the additive manufacturing system based on the transmitted information.

BRIEF DESCRIPTION OF THE DRAWINGS

FIG. 2A is a perspective view of a segment of a first example marked cylindrical filament, which includes encoded markings having sub-markings in a binary encoding scheme.

DETAILED DESCRIPTION

The present disclosure is directed to marked consumable materials for use in additive manufacturing systems (also referred to as direct digital manufacturing systems), such as extrusion-based digital manufacturing systems. The marked consumable materials include encoded markings that may contain a variety of information, such as information relating to properties of the marked consumable materials (e.g., physical and compositional properties) and information relating to parameters for operating the additive manufacturing systems (e.g., extrusion parameters).

The present disclosure is also directed sensor assemblies configured to read the encoded markings from successive portions of the marked consumable materials as the marked consumable materials are fed to the additive manufacturing systems. As discussed below, the sensor assemblies may transmit the information read from the encoded markings to one or more control components of the additive manufacturing systems. This allows the additive manufacturing systems to use the information in the encoded markings for a variety of different purposes, such as for building 3D models and/or support structures.

Figure 1:
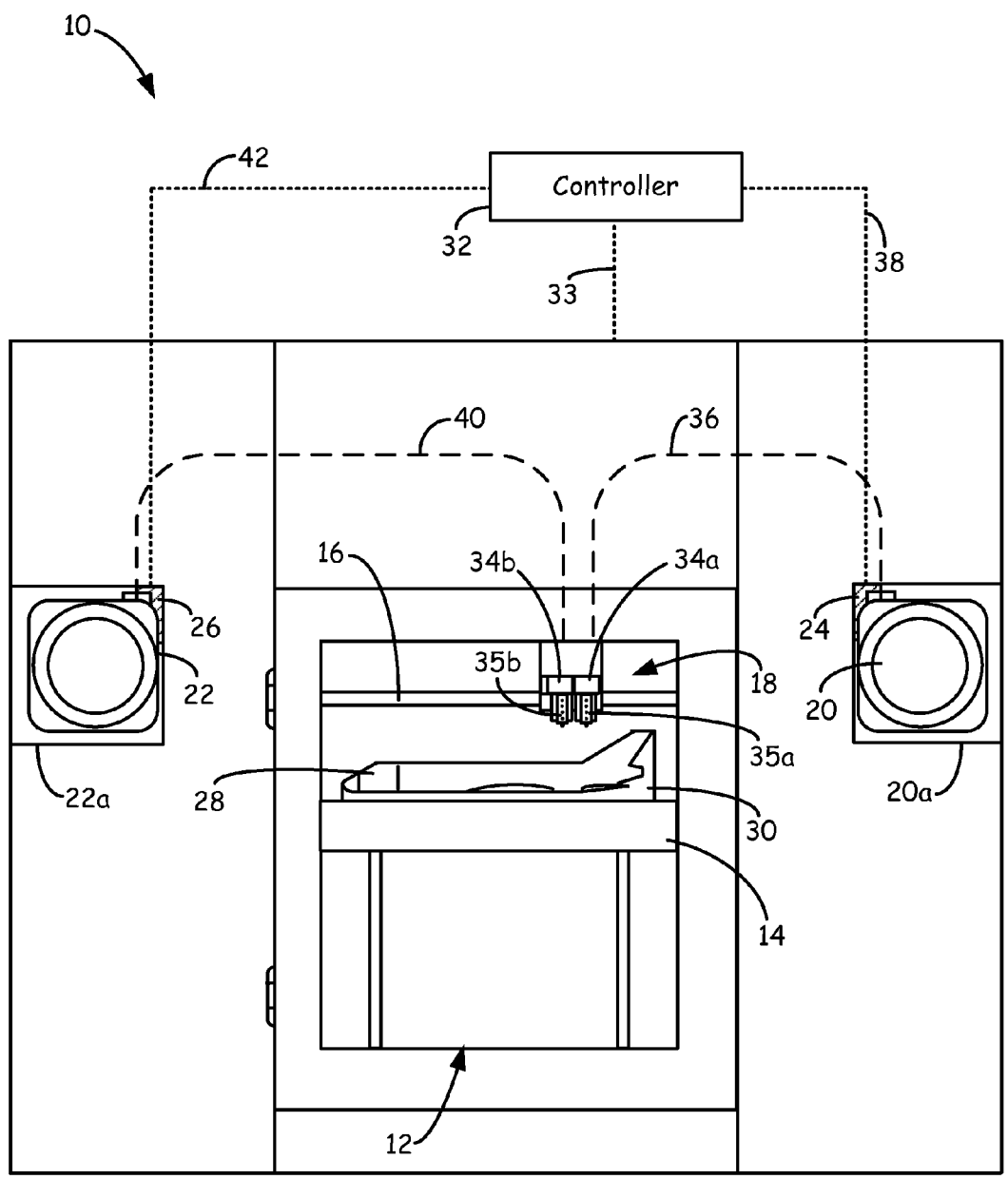
FIG. 1 is a front view of an extrusion-based additive manufacturing system for building 3D models and support structures from marked consumable materials having encoded markings.

FIG. 1 is a front view of system 10, which is an additive or direct digital manufacturing system, such as an extrusion-based additive manufacturing system. Suitable extrusion-based additive manufacturing systems for system 10 include fused deposition modeling systems developed by Stratasys, Inc., Eden Prairie, Minn. As shown, system 10 includes build chamber 12, platen 14, gantry 16, extrusion head 18, supply sources 20 and 22, and sensor assemblies 24 and 26, where sensor assemblies 24 and 26 are configured to read information from marked consumable materials (not shown in FIG. 1) provided in supply sources 20 and 22.

Build chamber 12 is an enclosed environment that contains platen 14, gantry 16, and extrusion head 18 for building a 3D model (referred to as 3D model 28) and a corresponding support structure (referred to as support structure 30). Build chamber 12 is desirably heated to reduce the rate at which the modeling and support materials solidify after being extruded and deposited.

Platen 14 is a platform on which 3D model 28 and support structure 30 are built, and moves along a vertical z-axis based on signals provided from a computer-operated controller (referred to as controller 32). As shown, controller 32 may communicate with build chamber 12, platen 14, gantry 16, and extrusion head 18 over communication line 33. While illustrated as a single signal line, communication line 33 may include one or more signal lines for allowing controller 33 to communicate with various components of system 10, such as build chamber 12, platen 14, gantry 16, and extrusion head 18.

Gantry 16 is a guide rail system configured to move extrusion head 18 in a horizontal x-y plane within build chamber 12 based on signals provided from controller 32 (via communication line 33). The horizontal x-y plane is a plane defined by an x-axis and a y-axis (not shown in FIG. 1), where the x-axis, the y-axis, and the z-axis are orthogonal to each other. In an alternative embodiment, platen 14 may be configured to move in the horizontal x-y plane within build chamber 12, and extrusion head 18 may be configured to move along the z-axis. Other similar arrangements may also be used such that one or both of platen 14 and extrusion head 18 are moveable relative to each other.

Extrusion head 18 is supported by gantry 16 for building 3D model 28 and support structure 30 on platen 14 in a layer-by-layer manner, based on signals provided from controller 32. Extrusion head 18 includes a pair of drive mechanisms 34a and 34b, and pair of liquefiers 35a and 35b configured to receive and melt successive portions of the marked consumable materials. Examples of suitable extrusion heads for extrusion head 18 include those disclosed in LaBossiere, et al., U.S. Patent Application Publication Nos. 2007/0003656 and 2007/00228590; Leavitt, U.S. Patent Application Publication No. 2009/0035405; and Batchelder et al., U.S. Pat. Nos. 8,439,665; 8,221,669; and 8,236,227. Alternatively, system 10 may include one or more two-stage pump assemblies, such as those disclosed in Batchelder et al., U.S. Pat. No. 5,764,521; and Skubic et al., U.S. Patent Application Publication No. 2008/0213419. Furthermore, system 10 may include a plurality of extrusion heads 18 for depositing modeling and/or support materials.

Supply sources 20 and 22 are devices configured to retain supplies of the marked consumable materials, and may be respectively loaded into bays 20a and 22a of system 10. In the shown embodiment, supply source 20 retains a supply of a marked modeling material and supply source 22 retains a supply of a marked support material. System 10 may also include additional drive mechanisms (not shown) configured to assist in feeding the marked consumable materials from supply sources 20 and 22 to extrusion head 18.

In some embodiments, the marked consumable materials may be provided to system 10 as filaments having marked exterior surfaces (not shown in FIG. 1), such as marked cylindrical filaments and/or marked non-cylindrical filaments, as discussed below. In these embodiments, suitable assemblies (e.g., spooled containers) for supply sources 20 and 22 include those disclosed in Swanson et al., U.S. Pat. No. 6,923,634; Comb et al., U.S. Pat. No. 7,122,246; Taatjes et al, U.S. Patent Application Publication Nos. 2010/0096485 and 2010/0096489; and Swanson, U.S. Pat. No. 8,403,658 and International Publication No. WO2009/088995.

In alternative embodiments, the marked consumable materials may be provided to system 10 as marked slugs or wafers, as discussed below. In these embodiments, suitable assemblies for supply sources 20 and 22 include those disclosed in Batchelder et al., U.S. Pat. No. 5,764,521.

Sensor assemblies 24 and 26 are configured to read the encoded markings of the marked consumable materials as the marked consumable materials are fed to extrusion head 18. Sensor assembly 24 may be retained at any suitable location between (or within) supply source 20 and extrusion head 18. Similarly, sensor assembly 26 may be retained at any suitable location between (or within) supply source 22 and extrusion head 18. In the shown example, sensor assemblies 24 and 26 are retained partially or fully within supply sources 20 and 22, respectively.

Figure 1A:
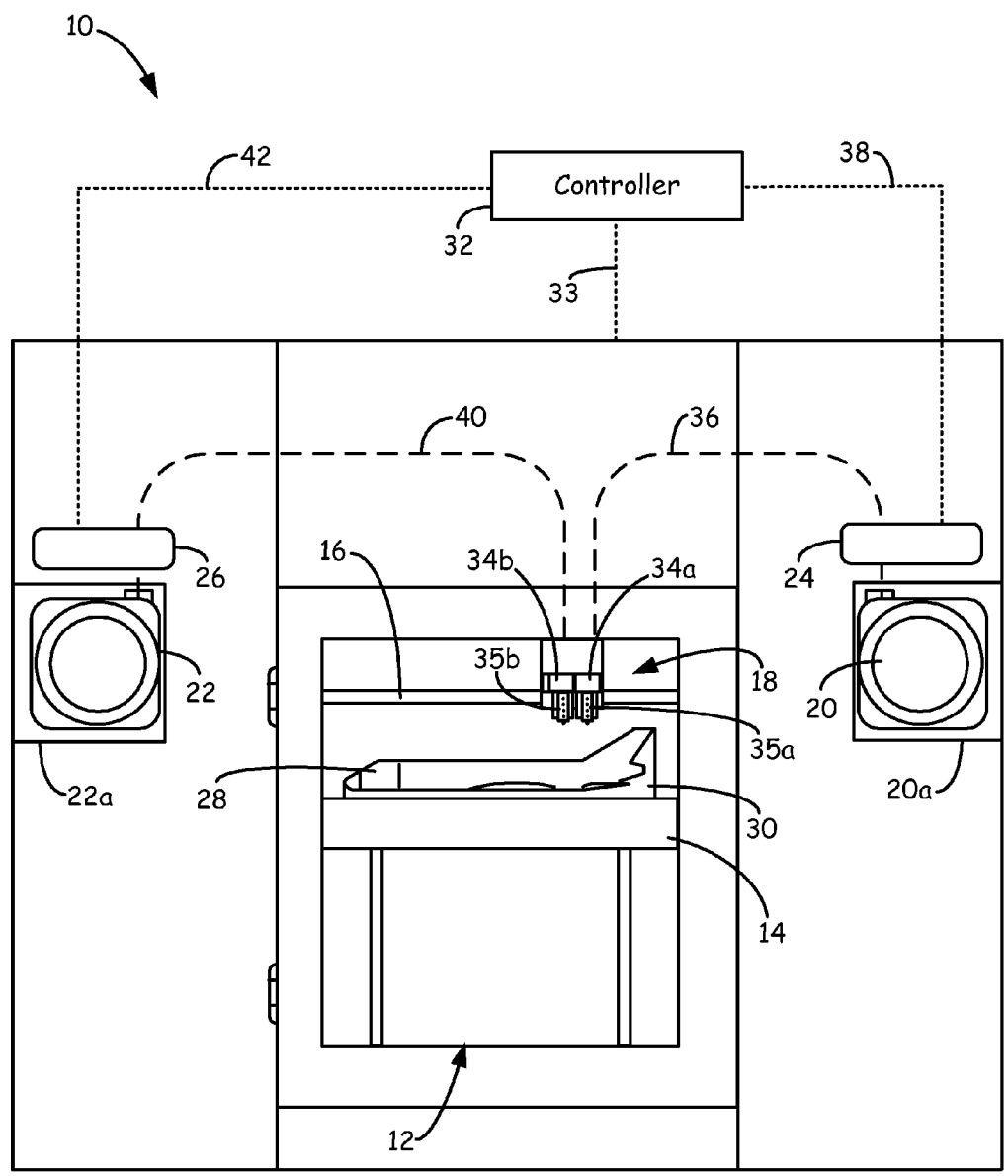
FIG. 1A is a front view of an alternative extrusion-based additive manufacturing system for building 3D models and support structures from marked consumable materials having encoded markings, which includes sensor assemblies retained along consumable material pathways of the system.

In alternative embodiments, as disclosed in U.S. Patent Publication No. 2011/0117268 and shown in FIG. 1A, sensor assemblies 24 and 26 may be retained along filament pathways within system 10 adjacent to supply sources 20 and 22, respectively. In further alternative embodiments, one or both of sensor assemblies 24 and 26 may be retained by gantry 16 with extrusion head 18, thereby moving sensor assemblies 24 and 26 with extrusion head 18.

As shown in FIG. 1, the marked modeling material may be provided to extrusion head 18 from supply source 20 through pathway 36, where pathway 36 may include a guide tube (not shown) for guiding the marked modeling material to extrusion head 18. In the shown embodiment, pathway 36 is downstream from sensor assembly 24, thereby allowing sensor assembly 24 to read the encoded information from the marked modeling material prior to passing through pathway 36. As further shown, sensor assembly 24 may communicate with controller 32 and/or any other control component of system 10 (e.g., a host computer system for system 10, not shown) over communication line 38. While illustrated as a single signal line, communication line 38 may include one or more signal lines for allowing sensor assembly 24 to communicate with one or more control components of system 10 (e.g., controller 32).

Similarly, the marked support material may be provided to extrusion head 18 from supply source 22 through pathway 40, where pathway 40 may also include a guide tube (not shown) for guiding the marked support material to extrusion head 18. In the shown embodiment, pathway 40 is downstream from sensor assembly 26, thereby allowing sensor assembly 26 to read the encoded information from the marked support material prior to passing through pathway 40. As further shown, sensor assembly 26 may communicate with controller 32 and/or any other control component of system 10 (e.g., the host computer system for system 10) over communication line 42. While illustrated as a single signal line, communication line 42 may include one or more signal lines for allowing sensor assembly 26 to communicate with one or more control components of system 10 (e.g., controller 32).

During a build operation, the marked consumable materials may be fed to extrusion head 18 through pathways 36 and 40. Sensor assemblies 24 and 26 may read the encoded markings of the marked consumable materials as successive portions of the marked consumable materials exit supply sources 20 and 22, and enter pathways 36 and 40. Information retained in the encoded markings may then be transmitted to controller 32 over communication lines 38 and 42, thereby allowing controller 32 to use the received information to assist in building 3D model 28 and/or support structure 30. For example, controller 32 may modify the extrusion parameters transmitted to extrusion head 18, allowing the thermal properties and/or the feed rates of extrusion head 18 to be adjusted based on the received information. In one embodiment, the thermal properties and/or the feed rates of extrusion head 18 may be adjusted based on received information relating to the cross sectional areas and/or the volumes of successive portions of the consumable materials.

Additionally, the received information may relate to the amount of the marked consumable materials remaining in supply source 20 or 22. This is beneficial for informing a user of system 10 how long the current supply of the marked consumable material will last before the user needs to load a new supply source to system 10. This information is particularly suitable for allowing the user to know if the build operation will end during a time period when the user may not necessarily be present to load a new supply source to system 10 (e.g., during overnight and/or weekend periods).

Furthermore, the received information may relate to the marked consumable material itself, such as the material type (e.g., modeling and support materials), material composition, and/or the material color. Sensor assemblies 24 and 26 may read these types of information from the marked consumable materials to confirm that the proper material was loaded to system 10, thereby reducing the risk of accidentally running system 10 with an incorrect material. For example, sensor assembly 24 may read information from the marked consumable material being fed from supply source 20, and controller 32 may confirm that the material being fed through pathway 36 is an intended modeling material, rather than a support material.

Combinations of the read information may also be used to assist in building 3D model 28 and/or support structure 30. For example, in embodiments in which bays 20a and 22a may each accept supply sources of modeling and support materials, the user may load supply source 20 of the marked modeling material into either bay 20a or bay 22a, and after the corresponding sensor assembly 24 or 26 reads the information from the marked consumable material, controller 32 may identify that the material is a modeling material for building 3D model 28 and adjust the extrusion parameters and feed rates accordingly. A similar arrangement may be accomplished with the marked support material in supply source 22. This prevents the user from having to load a particular supply source into a particular bay of system 10.

As the marked consumable materials are fed to extrusion head 18, gantry 16 may move extrusion head 18 around in the horizontal x-y plane within build chamber 12. Extrusion head 18 thermally melts the successive portions of the received marked modeling material, thereby allowing the molten modeling material to be extruded to build 3D model 28. Similarly, extrusion head 18 thermally melts the successive portions of the marked support material, thereby allowing the molten support material to be extruded to build support structure 30. The upstream, unmelted portions of the marked consumable materials may each function as a piston with a viscosity-pump action to extrude the molten material out of the respective liquefiers of extrusion head 18.

The extruded modeling and support materials are deposited onto platen 14 to build 3D model 28 and support structure 30 using a layer-based additive technique. Support structure 30 is desirably deposited to provide vertical support along the z-axis for overhanging regions of the layers of 3D model 28. After the build operation is complete, the resulting 3D model 28/support structure 30 may be removed from build chamber 12, and support structure 30 may be removed from 3D model 28. As used herein, the term "three-dimensional model" is intended to encompass any object built with an additive manufacturing system, and includes 3D models built from modeling materials (e.g., 3D model 28) as well a support structures built from support materials (e.g., support structure 30).

Figure 2:
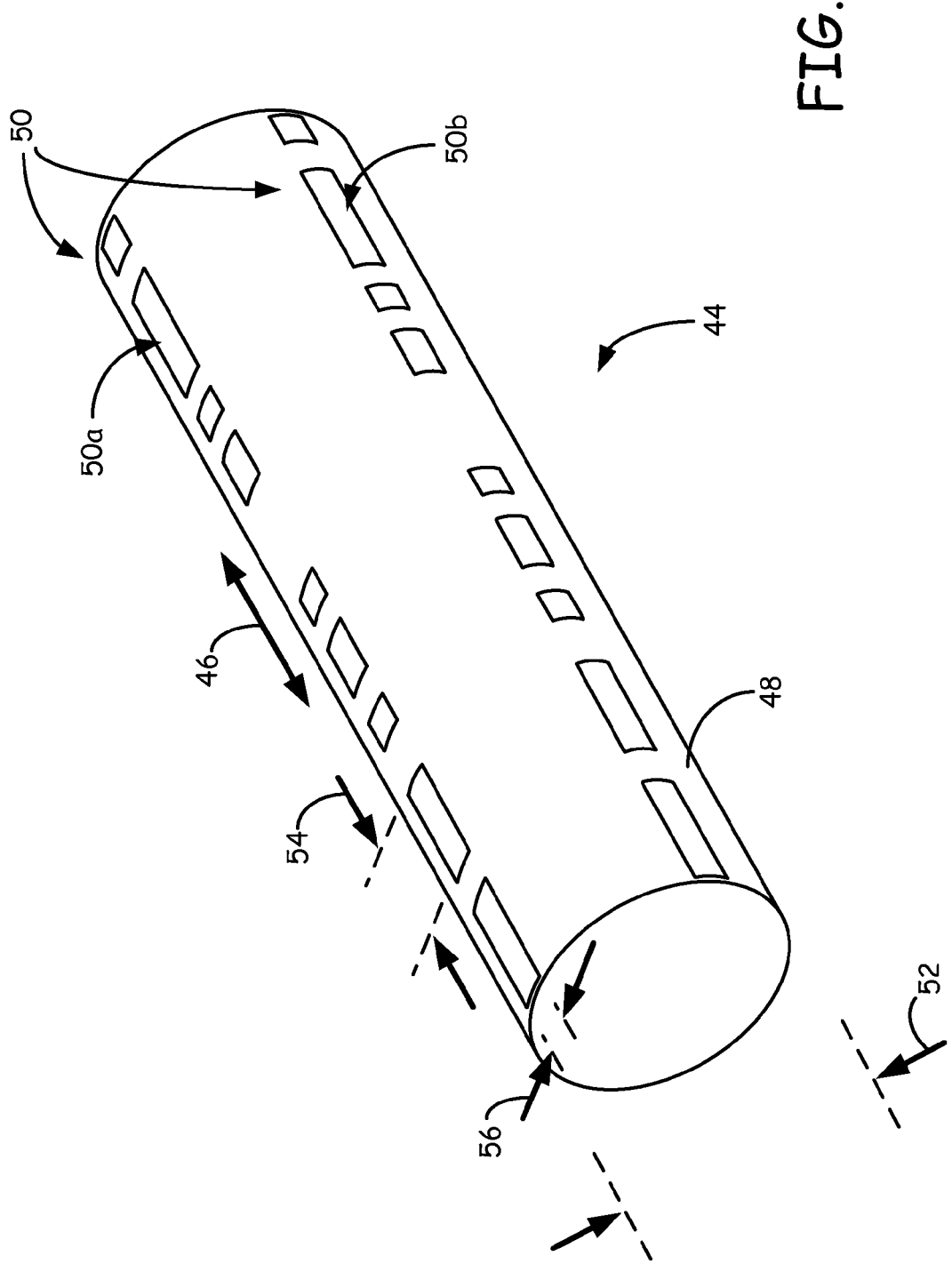
FIG. 2 is a perspective view of a segment of a marked cylindrical filament, which is an example of a marked consumable material for use in the extrusion-based additive manufacturing systems.

FIG. 2 illustrates a segment of filament 44, which is an example of a suitable marked consumable material of the present disclosure for use as a marked modeling material and/or a marked support material with system 10 (shown in FIG. 1). As shown in FIG. 2, filament 44 is a marked cylindrical filament having length 46, where length 46 is a continuous length that may vary depending on the amount of filament 44 remaining in supply source 20 or 22. While only a segment of filament 44 is illustrated in FIG. 2, it is understood that length 46 of filament 44 may extend for a substantial distance (e.g., greater than 25 meters).

Filament 44 also includes exterior surface 48 extending along length 46 and encoded markings 50, where encoded markings 50 are located at exterior surface 48 along at least a portion of length 46. In one embodiment, encoded markings 50 extend substantially along the entire length 46. Filament 44 also has a surface diameter (referred to as surface diameter 52) at a non-marked location that is desirably configured to allow filament 44 to mate with a liquefier of extrusion head 18 without undue friction. Examples of suitable average diameters for surface diameter 52 range from about 0.8 millimeters (about 0.03 inches) to about 2.5 millimeters (about 0.10 inches), with particularly suitable average diameters ranging from about 1.0 millimeter (about 0.04 inches) to about 2.3 millimeters (about 0.09 inches), and with even more particularly suitable average diameters ranging from about 1.3 millimeters (about 0.05 inches) to about 2.0 millimeters (about 0.08 inches).

In the shown embodiment, encoded markings 50 are trench-based markings in exterior surface 48 (e.g., via laser ablation). However, as discussed below, encoded markings 50 may alternatively be form on filament 44 using a variety of different marking techniques. For example, encoded markings 50 may be formed as coatings over exterior surface 48 via one or more coating processes (e.g., jetting and evaporation processes). Alternatively, encoded markings 50 may be formed by cross-linking the surface material of filament 44, such as with ultraviolet light, to vary the index of refraction of the material at encoded markings 50. Moreover, encoded markings 50 may be formed by jetting materials that are not readily visible to the naked eye but may be detected using a non-visible wavelength (e.g., ultraviolet-activated materials (e.g., fluorescent materials)). These are particularly suitable in embodiments in which encoded markings 50 function as diffraction gratings. Furthermore, the use of materials that are not readily visible to the naked eye is beneficial for reducing the impact of the encoded markings on the colors of the modeling and support materials.

Encoded markings 50 include encoded information, which may be read by sensor assembly 24 or 26 as successive portions of filament 44 pass through pathway 36 or 40 of system 10. As discussed above, the read information may then be transmitted to controller 32 over communication line 38 or 42, thereby allowing controller 32 to use the received information to assist in building 3D model 28 and/or support structure 30.

Encoded markings 50 may extend in multiple linear paths along length 46 (referred to as paths 50a and 50b), as shown. In this embodiment, encoded markings 50 may also include a third linear path (referred to as path 50c, not shown) such that paths 50a, 50b, and 50c are each separated by angles of about 120 degrees. This arrangement is beneficial for allowing sensor assembly 24 or 26 to read at least one of paths 50a, 50b, and 50c regardless of the axial orientation of filament 44 as successive portions of filament 44 pass through the given sensor assembly 24 or 26. In alternative embodiments, filament 44 may include fewer or additional paths of encoded markings 50 such that filament 44 includes at least one path of encoded markings 50 (e.g., paths 50a, 50b, and 50c). In additional alternative embodiments, one or more of the paths (e.g., paths 50a, 50b, and 50c) may extend along length 46 in a non-linear manner (e.g., S-curves and spiral arrangements).

Encoded markings 50 may include a variety of different information, such as information relating to filament 44 and/or system 10. Examples of suitable types of information that may be included in encoded markings 50 include local filament cross-sections (e.g., diameters and root-mean-square variations), volume increments, local and global filament extrusion parameters, length of filament 44 remaining in supply source 20 or 22, measurements of local filament fingerprint characteristics, material type (e.g., modeling and support materials), material composition, material color, manufacturing information for filament 44 (e.g., manufacturing dates, manufacturing locations, and lot numbers), product codes, material origin information, software and firmware updates for system 10, and combinations thereof.

In addition, encoded markings 50 may also include media-based information, such as operating and use instructions, artistic works (e.g., textual, video, and audio information), and the like. In these embodiments, system 10 may include capabilities for playing the encoded media, such as textual and/or graphical information that may be displayed for a user of system 10 to read, and/or audio information that may be played for a user of system 10 to hear. The amount of data per unit length along length 46 of filament 44 may vary depending on the particular marking technique used, the encoding scheme used, the dimensions of encoded markings 50, the number of encoded markings per unit length along length 46, the use of sub-markings (e.g., binary bits), and the like.

The dimensions and geometries of each mark of encoded markings 50 may vary depending on the encoding scheme and the marking technique used. In the current example in which encoded markings 50 are formed as trenches in exterior surface 48 (e.g., via laser ablation), encoded markings 50 desirably have small dimensions relative to the overall dimensions of filament 44 to minimize or otherwise reduce their impact on the diameter of filament 44. Additionally, as shown in the current embodiment, the trenches of encoded markings 50 have axial lengths (e.g., axial length 54) that vary to provide patterns based on the encoding scheme used. In alternative embodiments one or more of the radial widths of the marks (referred to as widths 56) and/or the depths of the marks may additionally or alternatively be varied to provide patterns based on the encoding scheme used.

Suitable average dimensions for width 56 range from about 51 micrometers (about 2 mils) to about 510 micrometers (about 20 mils), with particularly suitable average dimensions ranging from about 130 micrometers (about 5 mils) to about 250 micrometers (about 10 mils). Suitable dimensions for the axial lengths along length 46 (e.g., axial length 54) range from about 130 micrometers (about 5 mils) to about 5,100 micrometers (about 200 mils), with particularly suitable axial lengths ranging from about 1,300 micrometers (about 50 mils) to about 3,800 micrometers (about 150 mils).

Furthermore, suitable average depths of each mark of encoded markings 50 from exterior surface 48 range from about 1.3 micrometers (about 0.05 mils) to about 51 micrometers (about 2 mils), with particularly suitable average depths ranging from about 13 micrometers (about 0.5 mil) to about 38 micrometers (about 1.5 mils). As discussed below, the edges of the trench marks are suitable regions for scattering light in a darkfield illumination, which may allow an optical sensor assembly to read encoded markings 50 based on the patterns of the scattered light. In alternative embodiments, the encoded markings of filament 44 may be two-dimensional markings (e.g., coatings) rather than the three-dimensional geometry of encoded markings 50.

In further alternative embodiments, the axial lengths (e.g., axial length 54) and the radial widths (e.g., widths 56) of encoded markings 50 may be the same or substantially the same. In these embodiments, the patterns of encoded markings 50 along length 46 of filament 44 may vary to provide the encoding properties. For example, in embodiments in which encoded markings 50 function as diffraction gratings, encoded markings 50 may be formed as patterns of parallel lines having different indices of refraction from that of exterior surface 48. The parallel lines of encoded markings 50 may be the same or similar in geometry. However, the patterns of the parallel lines and the interstitial areas of exterior surface 48 may define the encoded pattern in filament 44.

Furthermore, each marking of encoded markings 50 may include one or more sub-marks, such as dot patterns suitable for encoding schemes. For example, as shown in FIG. 2A, each marking of encoded markings 50 may include a single dot corresponding to a "0" and two dots corresponding to a "1", or vice versa, representing a binary encoding scheme. As such, in this embodiment, each marking of encoded markings 50 may retain at least a portion of the encoded information, allowing multiple types of information to be encoded in encoded markings 50.

For example, in the shown binary-bit embodiment, the first dot of a dot pair may relate to a first type of encoded information (e.g., volume increments) and the binary pattern of single dots and dot pairs along length 46 may relate to a second type of encoded information. While the dot pairs are illustrated in FIG. 2A as extending along length 46, in an alternative embodiment, the dot pairs may extend in the radial direction.

Filament 44 referred to in FIGS. 2 and 2A may be manufactured from a variety of extrudable modeling and support materials for respectively building 3D model 28 and support structure 30. Suitable modeling materials for filament 44 include polymeric and metallic materials. In some embodiments, suitable modeling materials include materials having amorphous properties, such as thermoplastic materials, amorphous metallic materials, and combinations thereof. Examples of suitable thermoplastic materials for filament 44 include acrylonitrile-butadiene-styrene (ABS) copolymers, polycarbonates, polysulfones, polyethersulfones, polyphenylsulfones, polyetherimides, amorphous polyamides, modified variations thereof (e.g., ABS-M30 copolymers), polystyrene, and blends thereof. Examples of suitable amorphous metallic materials include those disclosed in Batchelder, U.S. Patent Application Publication No. 2009/0263582.

Suitable support materials for filament 44 include polymeric materials. In some embodiments, suitable support materials include materials having amorphous properties (e.g., thermoplastic materials) and that are desirably removable from the corresponding modeling materials after 3D model 28 and support structure 30 are built. Examples of suitable support materials for filament 44 include water-soluble support materials commercially available under the trade designations "SR10", "SR20", and "SR30" Soluble Supports from Stratasys, Inc., Eden Prairie, Minn.; break-away support materials commercially available under the trade designation "BASS" from Stratasys, Inc., Eden Prairie, Minn., and those disclosed in Crump et al., U.S. Pat. No. 5,503,785; Lombardi et al., U.S. Pat. Nos. 6,070,107 and 6,228,923; Priedeman et al., U.S. Pat. No. 6,790,403; and Hopkins et al., U.S. Patent Application Publication No. 2010/0096072.

The composition of filament 44 may also include additional additives, such as plasticizers, rheology modifiers, inert fillers, colorants, stabilizers, and combinations thereof. Examples of suitable additional plasticizers for use in the support material include dialkyl phthalates, cycloalkyl phthalates, benzyl and aryl phthalates, alkoxy phthalates, alkyl/aryl phosphates, polyglycol esters, adipate esters, citrate esters, esters of glycerin, and combinations thereof. Examples of suitable inert fillers include calcium carbonate, magnesium carbonate, glass spheres, graphite, carbon black, carbon fiber, glass fiber, talc, wollastonite, mica, alumina, silica, kaolin, silicon carbide, composite materials (e.g., spherical and filamentary composite materials), and combinations thereof. In embodiments in which the composition includes additional additives, examples of suitable combined concentrations of the additional additives in the composition range from about 1% by weight to about 10% by weight, with particularly suitable concentrations ranging from about 1% by weight to about 5% by weight, based on the entire weight of the composition.

Filament 44 also desirably exhibits physical properties that allow filament 44 to be used as a consumable material in system 10. For example, filament 44 is desirably flexible along length 46 to allow filament 44 to be retained in supply sources 20 and 22 (e.g., wound on spools) and to be fed through system 10 (e.g., through pathways 36 and 40) without plastically deforming or fracturing. For example, in one embodiment, filament 44 is capable of withstanding elastic strains greater than t/r, where "t" is a cross-sectional thickness of filament 44 in the plane of curvature, and "r" is a bend radius (e.g., a bend radius in supply source 20 or 22 and/or a bend radius through pathway 36 or 40).

In one embodiment, the composition of filament 44 is substantially homogenous along length 46. Additionally, the composition of filament 44 desirably exhibits a glass transition temperature that is suitable for use in build chamber 12. Examples of suitable glass transition temperatures at atmospheric pressure for the composition of filament 44 include temperatures of about 80° C. or greater. In some embodiments, suitable glass transition temperatures include about 100° C. or greater. In additional embodiments, suitable glass transition temperatures include about 120° C. or greater.

Filament 44 also desirably exhibits low compressibility such that its axial compression doesn't cause filament 44 to be seized within a liquefier. Examples of suitable Young's modulus values for the polymeric compositions of filament 44 include modulus values of about 0.2 gigapascals (GPa) (about 30,000 pounds-per-square inch (psi)) or greater, where the Young's modulus values are measured pursuant to ASTM D638-08. In some embodiments, suitable Young's modulus range from about 1.0 GPa (about 145,000 psi) to about 5.0 GPa (about 725,000 psi). In additional embodiments, suitable Young's modulus values range from about 1.5 GPa (about 200,000 psi) to about 3.0 GPa (about 440,000 psi).

Figure 2B:
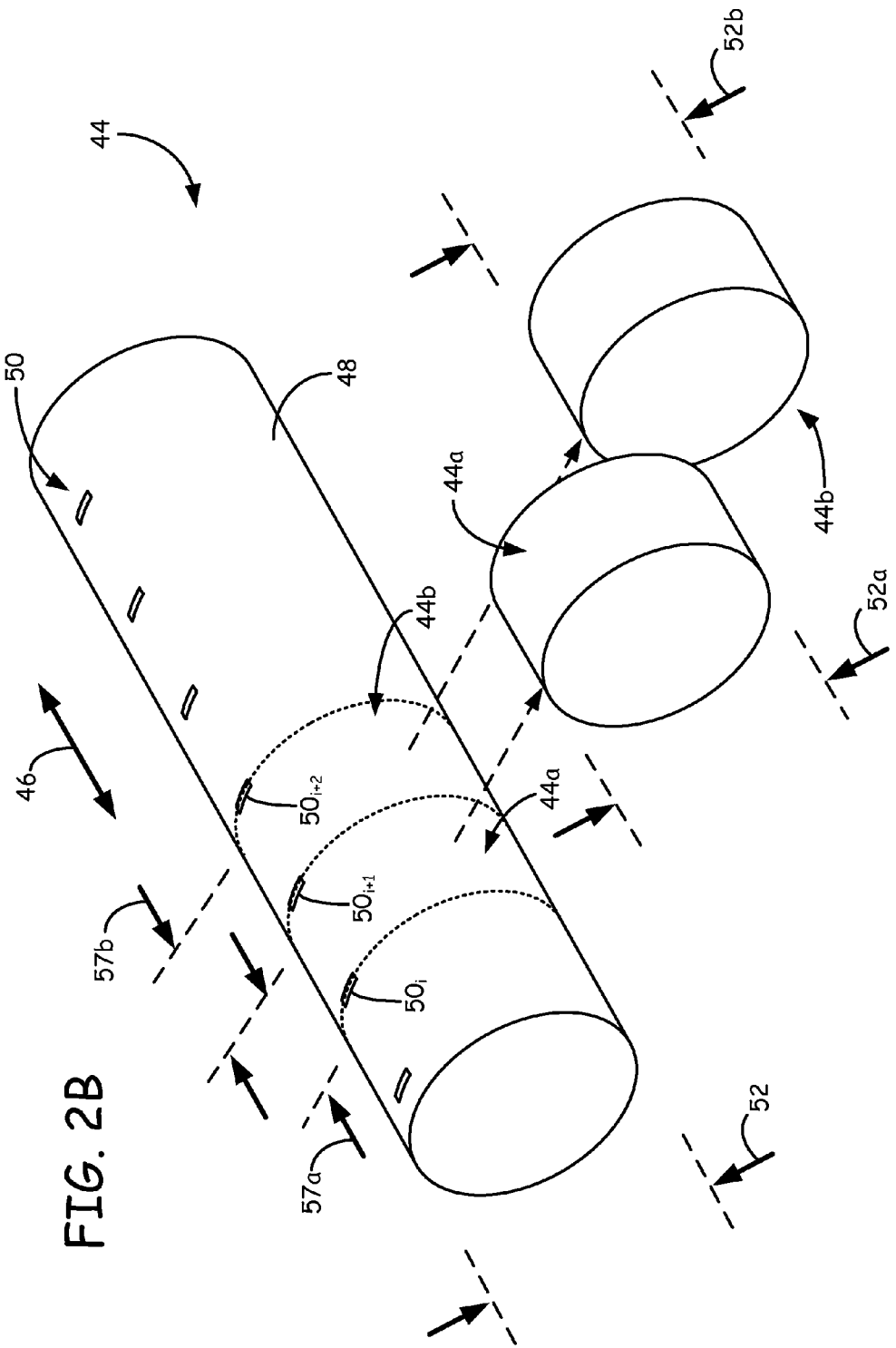
FIG. 2B is a perspective and partially exploded view of a segment of a second example marked cylindrical filament, which includes encoded markings denoting volume increments of the filament.

FIG. 2B illustrates an example embodiment of filament 44, in which encoded markings 50 designate volume increments of filament 44 along length 46. This is in comparison to length increments of filament 44 along length 46, which do not account for variations in the diameter or cross-sectional area of filament 44. As shown, each marking of encoded markings 50 may be offset along length 46 from a successive marking by distance denoting a volume increment (e.g., every 500 cubic micro-inches).

The volume of a given segment of filament 44 is the product of the cross-sectional area of filament 44 for the segment and the length of the segment along length 46. As such, in embodiments in which surface diameter 52 is constant along length 46, the distances between each marking of encoded markings 50 may be the same or substantially the same to maintain the same volume increment between each marking. However, in embodiments in which surface diameter 52 may vary along length 46 (e.g., fluctuations around a target diameter), the distances between each marking of encoded markings 50 may differ to maintain the same volume increment between each marking.

For example, as shown in FIG. 2B, encoded markings 50 extend along length 46, and include example markings $50_i$, $50_{i+1}$, and $50_{i+2}$. Marking $50_{i+1}$ is offset along length 46 from marking $50_i$ by distance 57a to define filament segment 44a, and marking $50_{i+2}$ is offset along length 46 from marking $50_{i+1}$ by distance 57b to define filament segment 44b. Filament segments 44a and 44b desirably have the same or substantially the same volumes, based on a predetermined volume increment. As such, if the average surface diameter 52 of filament segment 44a (referred to as surface diameter 52a) is the same as the average surface diameter 52 of filament segment 44b (referred to as surface diameter 52b), then lengths 57a and 57b may be the same to maintain the predetermined volume increment.

However, if surface diameter 52a of filament segment 44a is different from surface diameter 52b of filament segment 44b, then lengths 57a and 57b may differ to maintain the same predetermined volume increment. In particular, if surface diameter 52a of filament segment 44a is less than surface diameter 52b of filament segment 44b, then length 57a may be greater than length 57b by an extent such that the volumes of filament segments 44a and 44b are the same or substantially the same. Alternatively, if surface diameter 52a of filament segment 44a is greater than surface diameter 52b of filament segment 44b, then length 57a may be less than length 57b by an extent such that the volumes of filament segments 44a and 44b are the same or substantially the same.

As mentioned above, during a build operation, information retained in encoded markings 50 may be read by system 10 and transmitted to controller 32. In the embodiment shown in FIG. 2B, each marking of encoded markings 50 denotes a volume increment of the consumable material. Alternatively, each marking of encoded markings 50 may include sub-markings (e.g., dots for a binary encoding scheme), such that a portion of each marking of encoded markings 50 may denote the volume increment of the consumable material (and the binary pattern along length 46 may represent a second type of encoded information). With this information, controller 32 may modify the extrusion parameters transmitted to extrusion head 18, allowing the thermal properties and/or the feed rates of extrusion head 18 to be adjusted based on the received information.

For example, when sensor assembly 24 reads markings $50_i$ and $50_{i+1}$ and transmits the readings to controller 32, controller 32 may determine the duration between when sensor assembly 24 reads markings $50_i$ and $50_{i+1}$, and the feed rate of filament 44 during the determined duration. Based on this information controller 32 may direct drive mechanism 34a to adjust the feed rate of filament 44 when filament segment 44a reaches drive mechanism 34a.

Similarly, when sensor assembly 24 then reads marking $50_{i+2}$ and information may be transmitted to controller 32, and controller 32 may direct drive mechanism 34a to further adjust the feed rate of filament 44 when filament segment 44b reaches drive mechanism 34a (or drive mechanism 34b). This process may continue for each successive volume increment of filament 44, thereby increasing the control over the amounts of the consumable material extruded from extrusion head 18. Controlling the operation of system 10 based on the read volume increments provides greater control over the extrusion properties of the consumable material, and may compensate for variations in the cross-sectional areas of filament 44 along length 46. As such, system 10 may extrude precise volumes of the consumable material from liquefier assembly 34a (or liquefier assembly 34b), resulting in better part quality in 3D model 28 and/or support structure 30.

As discussed below, during the manufacture of filament 44 as shown in FIG. 2A, encoded markings 50 may be marked at exterior surface 48 using a variety of different techniques based on the volume increments. For example, encoded markings 50 may be marked with the use of a phase-lock-loop (PLL) control system, where the phases of the output marking locations along length 46 may be varied based on input diameter or cross-sectional area measurements.

In this embodiment, after the precursor for filament 44 is formed and solidified, the precursor may travel at a predetermined line speed, and the diameters or cross-sectional areas of the precursor may be measured over successive segments along length 46. These measured values may then be retained in one or more computer systems. As the precursor travels at the predetermined line speed, encoded markings 50 may then be formed at exterior surface 48 based on the measured diameters or cross-sectional areas. For example, encoded markings 50 may be formed by jetting materials that are not readily visible to the naked eye but may be detected using a non-visible wavelength (e.g., ultraviolet-activated materials). The PLL control system may vary the timing of the marking phase based on the measured diameters or cross-sectional areas to maintain the same or substantially the same volume increments of filament 44 between each successive marking. Furthermore, encoded markings 50 may alternatively include multiple paths (e.g., paths 50a, 50b, and 50c) as discussed above for the embodiment of filament 44 shown in FIGS. 2 and 2A.

The resulting filament 44 may then be wound up on a spool for subsequent storage and use in system 10. The above-discussed process allows filament 44 to be manufactured in a continuous process, where the precursor may be formed, solidified, measured, marked, and spooled in a continuous manner. In alternative embodiments, one or more of these steps may be performed in batch operations. For example, the measurement step may be performed separately from the marking step, where the measurements may be retained in one or more computer systems prior to being used with the PLL control system.

Figure 3:
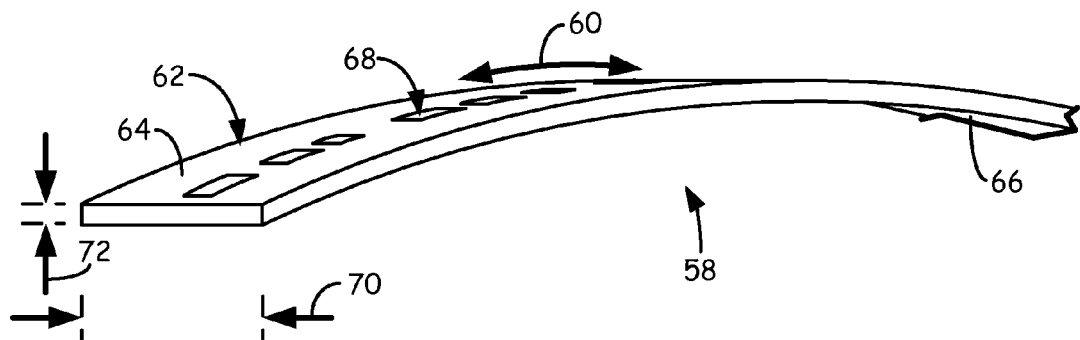
FIG. 3 is a perspective view of a segment of a marked non-cylindrical filament, which is an additional example of a marked consumable material for use in the extrusion-based additive manufacturing systems.

FIG. 3 illustrates a segment of filament 58, which is an additional example of a suitable marked consumable material of the present disclosure for use as a modeling material and/or a support material with system 10 (shown in FIG. 1). As shown in FIG. 3, filament 58 is a marked non-cylindrical filament having length 60, where length 60 is a continuous length that may vary depending on the amount of filament 58 remaining in supply source 20 or 22. While only a segment of filament 58 is illustrated in FIG. 3, it is understood that length 60 of filament 58 may extend for a substantial distance (e.g., greater than 25 meters).

Filament 58 also includes exterior surface 62 extending along length 60 and having major surfaces 64 and 66, which are the opposing major surfaces of filament 58. Filament 58 further includes encoded markings 68 located at major surface 64 of exterior surface 62, along at least a portion of length 60. In one embodiment, encoded markings 68 extend substantially along the entire length 60.

In the shown embodiment, encoded markings 68 are trench-based markings in exterior surface 62 (e.g., via laser ablation), as discussed above for encoded markings 50 of filament 44 (shown in FIG. 2). However, as discussed below, encoded markings 68 may alternatively be formed on filament 58 using a variety of different marking techniques (e.g., via one or more coating processes). For example, encoded markings 68 may be formed by cross-linking the surface material of filament 58, such as with ultraviolet light, to vary the index of refraction of the material at encoded markings 68. Moreover, encoded markings 68 may be formed by jetting materials that are not readily visible to the naked eye but may be detected using a non-visible wavelength (e.g., ultraviolet-activated materials). These are particularly suitable in embodiments in which encoded markings 68 function as diffraction gratings and/or as binary bits (with sub-marks).

Encoded markings 68 may extend in a single linear path along length 60 at major surface 64, as shown. In comparison to filament 44, which has a cylindrical cross section, filament 58 is less susceptible to axial rotation due to its rectangular cross section. As such, so long as filament 58 is provided to system 10 in the proper orientation, sensor assembly 24 or 26 may read encoded markings 68 as successive portions of filament 58 pass through the given sensor assembly 24 or 26. In an alternative embodiment, encoded markings 50 may also include an additional linear path along length 60 at major surface 66, and/or along the edges of filament 58. This embodiment allows sensor assembly 24 or 26 to read encoded markings 68 regardless of the orientation of filament 58. In additional alternative embodiments, filament 58 may include additional paths of encoded markings 68 at one or both of major surfaces 64 and 66. Furthermore, one or more of the paths of encoded markings 68 may extend along length 60 in a non-linear manner (e.g., S-curves and spiral arrangements).

Encoded markings 68 may include a variety of different information, such as information relating to filament 58 and/or system 10, which may be read by sensor assembly 24 or 26 in the same manner as discussed above for encoded markings 50 of filament 44. Accordingly, suitable types of information that may be retained in encoded markings 68 include those discussed above for encoded markings 50 (e.g., volume increments based on the cross-sectional areas along length 60).

Filament 58 has a cross section defined by width 70 and thickness 72, thereby defining a non-cylindrical cross section. Examples of suitable non-cylindrical filaments for filament 58 include those disclosed in Batchelder et al., U.S. Pat. Nos. 8,439,665; 8,221,669; and 8,236,227. Filament 58 is also desirably flexible along length 60 to allow filament 58 to be retained in supply sources 20 and 22 (e.g., wound on spools) and to be fed through system 10 (e.g., through pathways 36 and 40) without plastically deforming or fracturing. For example, in one embodiment, filament 58 is capable of withstanding elastic strains greater than t/r, where "t" is a cross-sectional thickness of filament 58 in the plane of curvature, and "r" is a bend radius (e.g., a bend radius in supply source 20 or 22 and/or a bend radius through pathway 36 or 40).

Examples of suitable average dimensions for width 70 range from about 1.0 millimeter (about 0.04 inches) to about 10.2 millimeters (about 0.40 inches), with particularly suitable average widths ranging from about 2.5 millimeters (about 0.10 inches) to about 7.6 millimeters (about 0.30 inches), and with even more particularly suitable average widths ranging from about 3.0 millimeters (about 0.12 inches) to about 5.1 millimeters (about 0.20 inches).

Examples of suitable average dimensions for thickness 72 range from about 0.08 millimeters (about 0.003 inches) to about 1.5 millimeters (about 0.06 inches), with particularly suitable average thicknesses ranging from about 0.38 millimeters (about 0.015 inches) to about 1.3 millimeters (about 0.05 inches), and with even more particularly suitable average thicknesses ranging from about 0.51 millimeters (about 0.02 inches) to about 1.0 millimeter (about 0.04 inches).

Examples of suitable aspect ratios of width 70 to thickness 72 include aspect ratios greater than about 2:1, with particularly suitable aspect ratios ranging from about 2.5:1 to about 20:1, and with even more particularly suitable aspect ratios ranging from about 3:1 to about 10:1.

The dimensions and geometries of each mark of encoded markings 68 may also vary depending on the encoding scheme and the marking technique used. In the current example in which encoded markings 68 are formed as trenches in exterior surface 62 (e.g., via laser ablation), encoded markings 68 desirably have small dimensions relative to the overall dimensions of filament 58 to minimize or otherwise reduce their impact on the cross sectional area of filament 58.

Additionally, as shown in the current embodiment, the trenches of encoded markings 68 have axial lengths (along length 60) that vary to provide patterns based on the encoding scheme used. In alternative embodiments one or more of the widths of the marks (along width 70) and/or the depths of the marks (along thickness 72) may additionally or alternatively be varied to provide patterns based on the encoding scheme used. Examples of suitable axial lengths, widths, and depths for each mark of encoded markings 68 include those discussed above for encoded markings 50 of filament 44.

Furthermore, the axial lengths along length 60 and the widths along widths 70 of encoded markings 68 may be the same or substantially the same. In these embodiments, the patterns of encoded markings 68 along length 60 of filament 58 may vary to provide the encoding properties. For example, in embodiments in which encoded markings 68 function as diffraction gratings, encoded markings 68 may be formed as patterns of parallel lines having different indices of refraction from that of major surface 64 and/or major surface 66. The parallel lines of encoded markings 68 may be the same or similar in geometry. However, the patterns of the parallel lines and the interstitial areas of major surface 64 and/or major surface 66 may define the encoded pattern in filament 58.

Alternatively, each marking of encoded markings 68 may include sub-markings (e.g., dots for a binary encoding scheme). In this embodiment, a portion of each marking of encoded markings 68 may denote a first type of encoded information (e.g., volume increments), and the binary pattern along length 60 may represent a second type of encoded information.

Filament 58 may also be manufactured from a variety of extrudable modeling and support materials for respectively building 3D model 28 and support structure 30. Examples of suitable modeling and support materials include those discussed above for filament 44. Filament 58 also desirably exhibits physical properties that allow filament 58 to be used as a consumable material in system 10. In one embodiment, the composition of filament 58 is substantially homogenous along length 60. Additionally, the composition of filament 58 desirably exhibits a glass transition temperature that is suitable for use in build chamber 12. Examples of suitable glass transition temperatures at atmospheric pressure for the composition of filament 58 include those discussed above for filament 44. Filament 58 also desirably exhibits low compressibility such that its axial compression doesn't cause filament 58 to be seized within a liquefier. Examples of suitable Young's modulus values for the polymeric compositions of filament 58 include those discussed above for filament 44.

Figure 4:
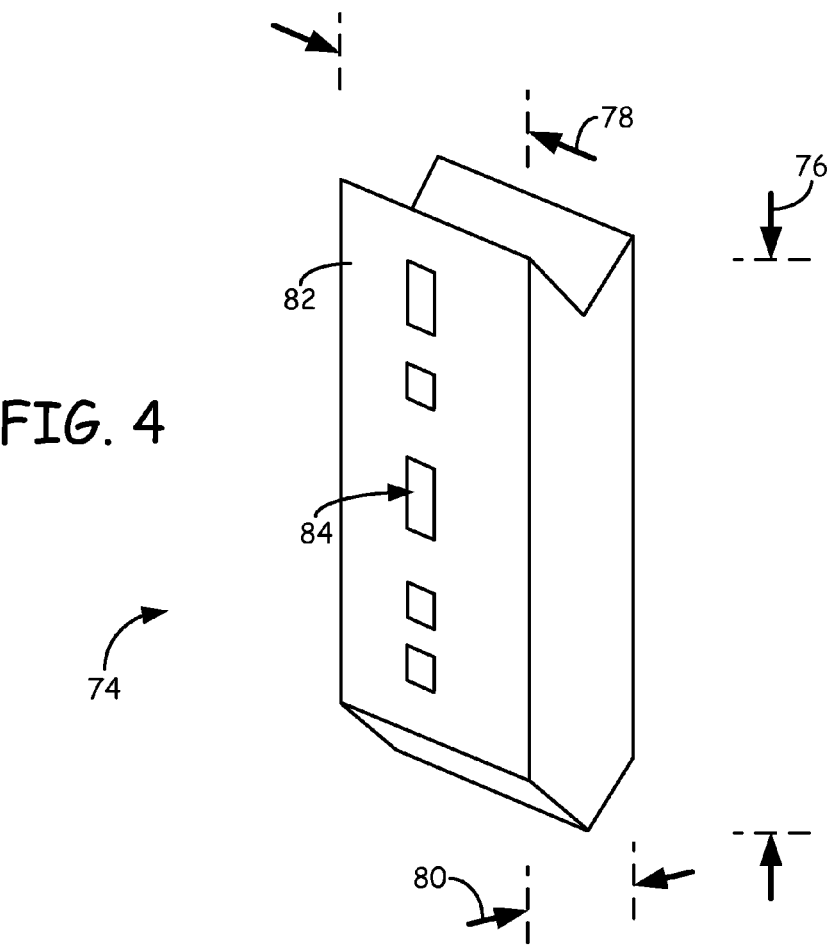
FIG. 4 is a perspective view of a marked slug or wafer, which is an additional example of a marked consumable material for use in the extrusion-based additive manufacturing systems.

FIG. 4 illustrates slug or wafer 74, which is an additional example of a suitable marked consumable material of the present disclosure for use as a modeling material and/or a support material with system 10 (shown in FIG. 1). As shown in FIG. 4, slug 74 dimensionally includes length 76, width 78, and thickness 80. Examples of suitable designs for slug 74 include those disclosed in Batchelder et al., U.S. Pat. No. 5,764,521. Accordingly, a series of slugs 74 may be fed through pathway 36 or 40 in an end-to-end arrangement to provide slugs 74 to extrusion head 18.

Slug 74 also includes exterior surface 82 extending along length 76, and encoded markings 84 located at exterior surface 82, along at least a portion of length 76. In one embodiment, encoded markings 84 extend substantially along the entire length 86. In the shown embodiment, encoded markings 84 are trench-based markings in exterior surface 82 (e.g., via laser ablation), as discussed above for encoded markings 50 of filament 44 (shown in FIG. 2). However, as discussed below, encoded markings 84 may alternatively be written to slug 74 using a variety of different marking techniques (e.g., via one or more coating processes). For example, encoded markings 84 may be formed by cross-linking the surface material of slug 74, such as with ultraviolet light, to vary the index of refraction of the material at encoded markings 84. Moreover, encoded markings 84 may be formed by jetting materials that are not readily visible to the naked eye but may be detected using a non-visible wavelength (e.g., ultraviolet-activated materials). This is particularly suitable in embodiments in which encoded markings 84 function as diffraction gratings and/or as binary bits (with sub-marks).

Encoded markings 84 may extend in a single linear path along length 76 at one or both major surfaces of exterior surface 82, as shown. In additional alternative embodiments, slug 74 may include additional paths of encoded markings 84 at one or both of major surfaces of exterior surface 82. Furthermore, one or more of the paths of encoded markings 84 may extend along length 76 in a non-linear manner (e.g., S-curves and spiral arrangements).

Encoded markings 84 may also include a variety of different information, such as information relating to slug 74 and/or system 10, which may be read by sensor assembly 24 or 26 in the same manner as discussed above for encoded markings 50 of filament 44. Accordingly, suitable types of information that may be retained in encoded markings 84 include those discussed above for encoded markings 50 (e.g., volume increments based on the cross-sectional areas along length 76).

Examples of suitable average dimensions for length 76 range from about 25 millimeters (about 1.0 inch) to about 150 millimeters (about 6.0 inches), with particularly suitable average lengths ranging from about 38 millimeters (about 1.5 inches) to about 76 millimeters (about 3.0 inches), and with even more particularly suitable average lengths ranging from about 43 millimeters (about 1.7 inches) to about 64 millimeters (about 2.5 inches).

Examples of suitable average dimensions for width 78 range from about 10 millimeters (about 0.4 inches) to about 38 millimeters (about 1.5 inches), with particularly suitable average widths ranging from about 13 millimeters (about 0.5 inches) to about 33 millimeters (about 1.3 inches), and with even more particularly suitable average widths ranging from about 15 millimeters (about 0.6 inches) to about 25 millimeters (about 1.0 inch).

Examples of suitable average dimensions for thickness 80 range from about 1.3 millimeters (about 0.05 inches) to about 13 millimeters (about 0.5 inches), with particularly suitable average thicknesses ranging from about 2.5 millimeters (about 0.1 inches) to about 7.6 millimeters (about 0.3 inches), and with even more particularly suitable average thicknesses ranging from about 3.8 millimeters (about 0.15 inches) to about 6.4 millimeters (about 0.25 inches).

The dimensions and geometries of each mark of encoded markings 84 may also vary depending on the encoding scheme and the marking technique used. In the current example in which encoded markings 84 are formed as trenches in exterior surface 82 (e.g., via laser ablation), encoded markings 84 desirably have small dimensions relative to the overall dimensions of slug 74 to minimize or otherwise reduce their impact on the cross sectional area of slug 74.

Additionally, as shown in the current embodiment, the trenches of encoded markings 84 have axial lengths (along length 76) that vary to provide patterns based on the encoding scheme used. In alternative embodiments one or more of the widths of the marks (along width 78) and/or the depths of the marks (along thickness 80) may additionally or alternatively be varied to provide patterns based on the encoding scheme used. Examples of suitable axial lengths, widths, and depths for each mark of encoded markings 84 include those discussed above for encoded markings 50 of filament 44.

Furthermore, the axial lengths and the widths of encoded markings 84 may be the same or substantially the same. In these embodiments, the patterns of encoded markings 84 along the length of slug 74 may vary to provide the encoding properties. For example, in embodiments in which encoded markings 84 function as diffraction gratings, encoded markings 84 may be formed as patterns of parallel lines having different indices of refraction from that of exterior surface 82. The parallel lines of encoded markings 84 may be the same or similar in geometry. However, the patterns of the parallel lines and the interstitial areas of exterior surface 82 may define the encoded pattern in slug 74.

Alternatively, each marking of encoded markings 84 may include sub-markings (e.g., dots for a binary encoding scheme). In this embodiment, a portion of each marking of encoded markings 84 may denote a first type of encoded information (e.g., volume increments), and the binary pattern along the length of slug 74 may represent a second type of encoded information.

Slug 74 may also be manufactured from a variety of extrudable modeling and support materials for respectively building 3D model 28 and support structure 30. Examples of suitable modeling and support materials include those discussed above for filament 44. Slug 74 also desirably exhibits physical properties that allow slug 74 to be used as a consumable material in system 10. In one embodiment, the composition of slug 74 is substantially homogenous along length 76. Additionally, the composition of slug 74 desirably exhibits a glass transition temperature that is suitable for use in build chamber 12. Examples of suitable glass transition temperatures at atmospheric pressure for the composition of slug 74 include those discussed above for filament 44. Slug 74 also desirably exhibits low compressibility such that its axial compression doesn't cause slug 74 to be seized within a liquefier. Examples of suitable Young's modulus values for the polymeric compositions of slug 74 include those discussed above for filament 44.

In addition to the above-discussed marked consumable material geometries, the marked consumable materials of the present disclosure include a variety of geometries, such as pellet geometries, irregular geometries, and the like. For example, the marked consumable materials may be provided as pellets with one or more linear encodings formed on the exterior surfaces of the pellets as discussed above for filament 44, filament 58, and slug 74. Examples of suitable pellet geometries include pellets having length-to-cross section (e.g., length-to-diameter) ratios ranging from about 1:1 to about 10:1. In some embodiments, suitable length-to-cross section ratios range from about 2:1 to about 5:1. The pellets may also include random fractured portions, such as random fractured ends.

Examples of suitable average cross sectional areas for the pellets range from about 0.2 square-millimeters to about 15 square-millimeters, with particular suitable average cross sectional areas ranging from about 0.75 square-millimeters to about 5 square millimeters. In embodiments in which the pellets have somewhat cylindrical cross sections, examples of suitable average diameters range from about 0.5 millimeters to about 4 millimeters, with particularly suitable average diameters ranging from about 1 millimeter to about 2 millimeters. Examples of suitable average lengths for the pellets range from about 1 millimeter to about 20 millimeters, with particularly suitable average lengths ranging from about 2 millimeters to about 10 millimeters.

Figure 5:
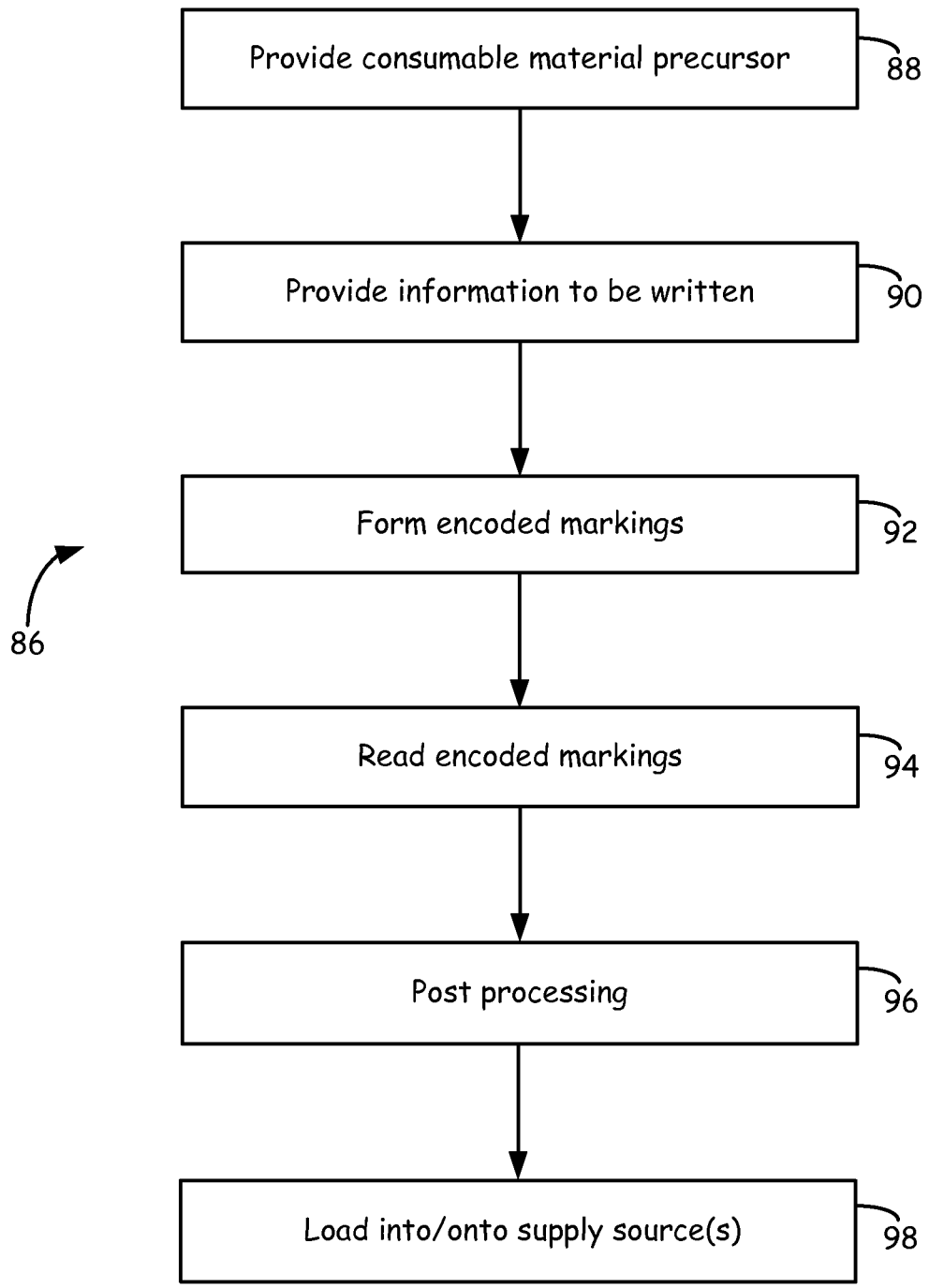
FIG. 5 is a flow diagram of a method for manufacturing marked consumable materials.

FIG. 5 is a flow diagram of method 86 for manufacturing the marked consumable materials of the present disclosure, such as filament 44 (shown in FIG. 2), filament 58 (shown in FIG. 3), and slug 74 (shown in FIG. 4). Method 58 includes steps 88-98, and initially involves providing a consumable material precursor, which is the consumable material in an unmarked state (step 88). For example, the precursor may be provided as a prefabricated material (e.g., filament or slug) in a solid state (e.g., retained on a supply source). Alternatively, the precursor may be provided by extruding the modeling or support material to form the precursor.

Examples of suitable techniques for forming the precursor for filament 44 include those disclosed in Comb. et al., U.S. Pat. Nos. 6,866,807 and 7,122,246. Examples of suitable techniques for forming the precursor for filament 58 include those disclosed in Batchelder et al., U.S. Pat. No. 8,221,669. Examples of suitable techniques for forming the precursor for slug 74 include those disclosed in Batchelder et al., U.S. Pat. No. 5,764,521. Additional examples of suitable techniques for forming the precursor with topographical surface patterns configured to engage with a filament drive mechanism of system 10 include those disclosed in Batchelder et al., U.S. Pat. No. 8,236,227.

The information to be written to the precursor as encoded markings may also be provided (step 90). For example, the information may be retained in one or more computer systems prior to being written to the precursor. In one embodiment in which the information includes physical properties of the precursor, such as the local filament cross-sections (e.g., diameters and root-mean-square variations) and/or volume increments, this information may be obtained by measuring the precursor and storing the measurements in one or more computer systems prior to being written to the precursor as encoded markings. For example, after the precursor of filament 44 is extruded and solidified, the diameters of successive portions of filament 44 may be measured and stored for subsequent writing as at least a portion of encoded markings 50. Correspondingly, after the precursor of filament 58 is extruded and solidified, the cross-sectional areas of successive portions of filament 58 may be measured and stored for subsequent writing as at least a portion of encoded markings 68.

The encoded markings (e.g., encoded markings 50, 68, and 84) may then be formed at the exterior surface while the precursor is at least partially solidified (step 92). In one embodiment, the encoded markings are formed at the exterior surface while the precursor is fully solidified. The pattern of the encoded markings may be based on the information being written, the encoding scheme used, and the device used to mark the precursor. A variety of encoding schemes may be used, where the encoding scheme desirably allows the encoded markings to be written to the precursor without substantially reducing line speeds. Examples of suitable average line speeds for manufacturing the marked consumable materials include line speeds up to about 20 meters/second (about 750 inches/second), with particularly suitable average line speeds ranging from about 1.3 meters/second (about 50 inches/second) to about 5 meters/second (about 200 inches/second). Additionally, the encoding scheme also desirably allows the encoded markings to be read by sensor assembly 24 or 26 in system 10 without substantially affecting the drive rate of the marked consumable material to extrusion head 18.

In embodiments in which the encoded markings at least partially denote volume increments along the consumable material (e.g., filaments 50 and 68, and slug 74), the encoded markings may be formed at the exterior surface using a variety of different techniques based on the volume increments. For example, as discussed above, the encoded markings may be marked with the use of a phase-lock-loop (PLL) control system, where the phases of the output marking locations along the length may be varied based on input diameter or cross-sectional area measurements.

As also discussed above, controlling the operation of system 10 based on the read volume increments provides greater control over the extrusion properties of the consumable materials, and may compensate for variations in the diameters or cross-sectional areas of the consumable materials. As such, system 10 may extrude precise volumes of the consumable materials from liquefier assembly 34a (or liquefier assembly 34b), resulting in better part quality in 3D model 28 and/or support structure 30.

As discussed above, the encoded markings may be formed by jetting materials that are not readily visible to the naked eye but may be detected using a non-visible wavelength (e.g., ultraviolet-activated materials). Alternatively, encoded markings 50, 68, and 84 may be formed as trench-based markings in the precursor. The trenches may be formed within the exterior surface of the precursor using a variety of techniques, such as laser ablation, physical imprinting, chemical etching (e.g., with masking), and combinations thereof. Due to the small dimensions and materials of the precursor, the particular technique used to form the trenches of the encoded markings is desirably selected to reduce the risk of significantly damaging or cracking the precursor while forming the trenches. As discussed below, the edges of the trench marks are suitable regions for scattering light in a darkfield illumination, which may allow an optical sensor assembly to read the encoded markings based on the patterns of the scattered light.

A suitable laser ablation technique for forming the encoded markings as trenches in the exterior surface of the precursor may be performed with an ultraviolet laser, such as an excimer laser. An excimer laser may remove material from the exterior surface of the precursor without significant damage or cracking to the underlying material of the precursor. Furthermore, excimer light may be strongly absorbed such that the surface material may be converted to vapor, leaving a trench without micro-cracks or residual ash. This embodiment is also beneficial for forming the encoded markings in a continuous manner, in which successive portions of the precursor may be exposed to the excimer laser.

Alternatively, the encoded markings may be formed with a variety of different processes. In one embodiment, the encoded markings may be formed with one or more coating processes, which may form the encoded markings on the exterior surface of the precursor as coatings that may be optically detected. For example, the coatings may be formed with a jetting, deposition, or evaporation process, where the coating is desirably formed with a material that is not readily visible to the naked eye but may be detected using a non-visible wavelength (e.g., ultraviolet-activated materials). In these embodiments, the sensor assembly (e.g., sensor assemblies 24 and 26) may emit light in one or more non-visible wavelengths and detect the light emitted from the activated materials of the encoded markings. These embodiments are beneficial for reducing the impact of the encoded markings on the colors of the modeling and support materials.

In additional alternative embodiments, the encoded markings may be formed by one or more mechanical impression processes, such as by mechanically impressing the pattern into the surface, such as with an agile stylus, rotating die, a recycling belt, and the like. The exterior surface may also be machined, skived, ground, polished, and the like. Furthermore, the encoded markings may be produced by one or more surface property modification processes, such as by modifying the surface properties of the precursor material. For example, the degree of cross linking of the precursor material may be locally modified by ultraviolet light to varying the index of refraction. In this embodiment, the encoded markings may be generated as lines (e.g., parallel lines) of cross-linked precursor material having different indices of refraction from the remaining surface of the consumable material. As discussed below, this embodiment is particularly suitable for use as diffraction gratings with a sensor assembly configured to read information based on far-field diffraction patterns generated from the diffraction gratings. Ion implantation can similarly modify the local complex index.

After a particular segment of the precursor is marked with the encoded markings to form the marked consumable material, the recently formed encoded markings may optionally be read with a sensor assembly to ensure that the information in the encoded markings is accurate (step 94). If the information is determined to be accurate, the marked consumable material may optionally undergo one or more post-processing operations (step 96), and then may be loaded into or onto a supply source (e.g., supply sources 20 and 22) for subsequent use in an additive manufacturing system (e.g., system 10) (step 98).

In alternative embodiments, steps 94, 96, and 98 may be performed in different orders and/or one or both of steps 94 and 96 may be omitted.

Figure 6:
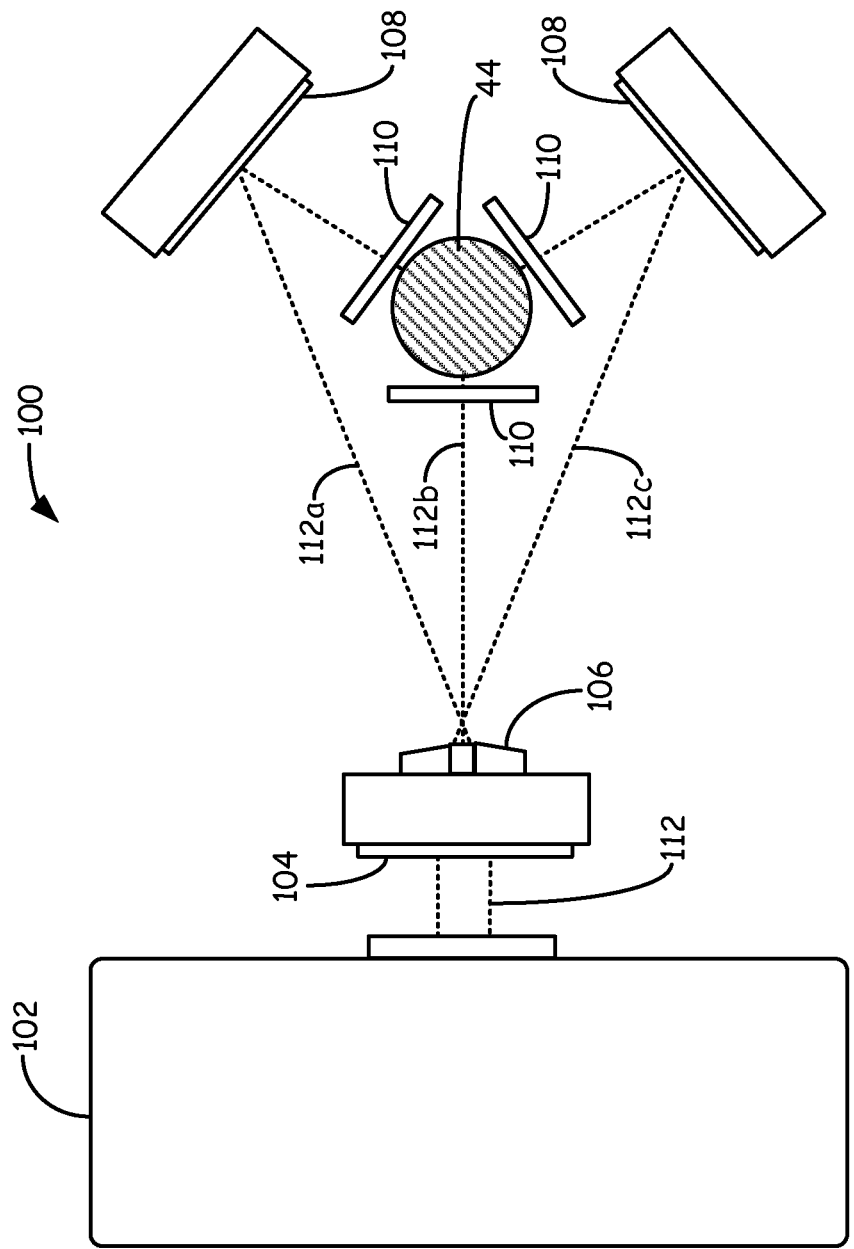
FIG. 6 is a schematic illustration of a laser marking system configured to form encoded markings in consumable materials.
Figure 7:
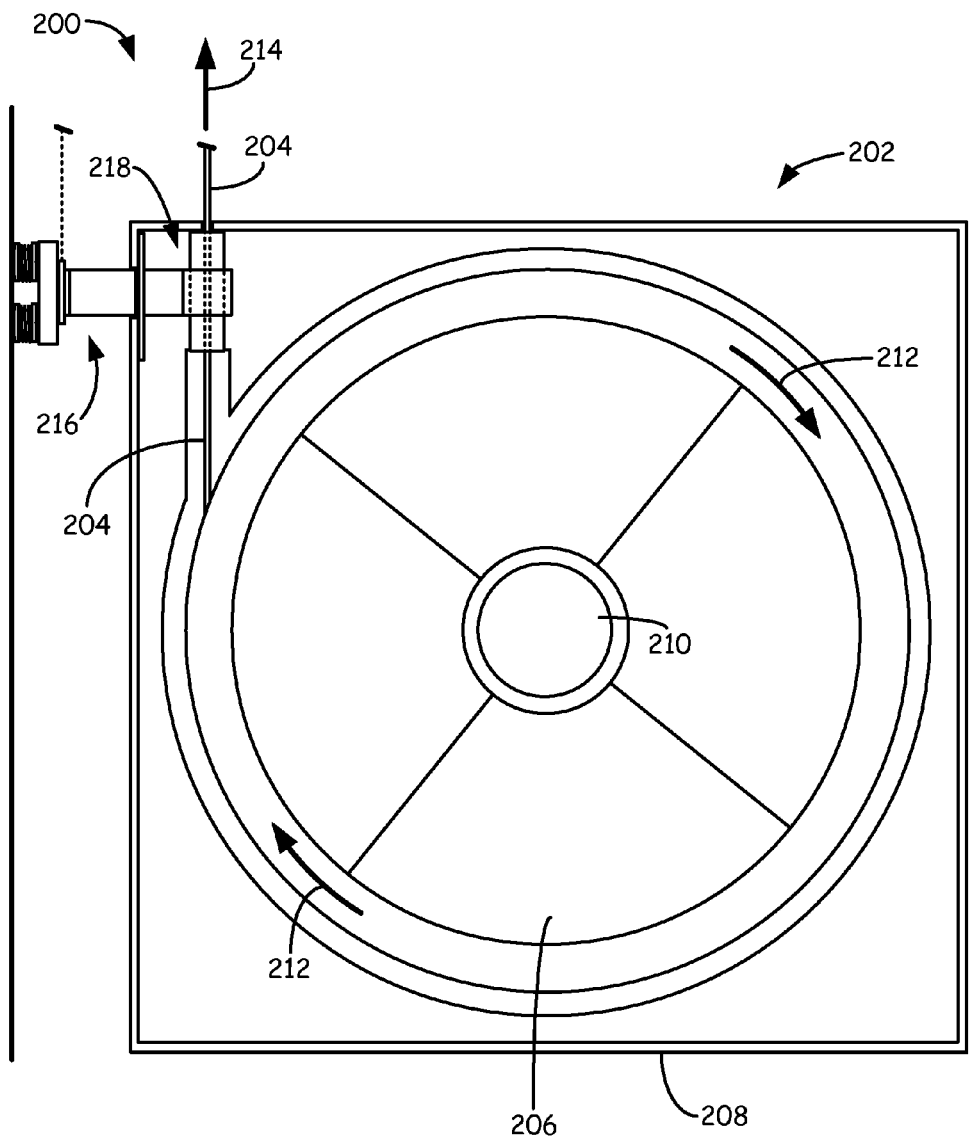
FIG. 7 is a schematic illustration of a sensor assembly of one embodiment of the present disclosure in use with a spooled container, where the sensor assembly contains a first subassembly located within an extrusion-based additive manufacturing system and a second subassembly located within a spooled container.

FIG. 6 is a schematic illustration of marking system 100, which is an example of a suitable laser marking system for forming encoded markings in a consumable material precursor, pursuant to step 92 of method 86 (shown in FIG. 5). The following discussion of marking system 100 is made with reference to filament 44 (shown in FIG. 2) with the understanding that marking system 100 may also be modified for forming encoded markings for a variety of marked consumable materials of the present disclosure (e.g., filament 58 shown in FIG. 3, and slug 74 shown in FIG. 4).

As shown in FIG. 6, marking system 100 is a laser ablation system (e.g., an excimer laser ablation system) that includes laser source 102, encoder mask 104, beam splitter 106, reflectors 108, and slot apertures 110. Laser source 102 is a laser emission source (e.g., an excimer laser source) for emitting laser beam 112 toward dielectric mask 104. In one embodiment, laser source 102 is configured to emit laser beam 112 having an ultraviolet-radiation wavelength. In another embodiment, the wavelength for laser beam 112 ranges from about 100 nanometers to about 400 nanometers. In yet another embodiment, the wavelength for laser beam 112 ranges from about 150 nanometers to about 300 nanometers.

Laser source 102 also desirably emits laser beam 112 with an energy level that is sufficient to form the trenches of encoded markings 50 in the material of the precursor for filament 44, while also desirably being low enough to reduce the risk of significantly damaging or cracking the precursor while forming the trenches. Examples of suitable energy levels per pulse of laser beam 112, based on a pulse length of about 8 nanoseconds, range from about 4 millijoules to about 20 millijoules, with particularly suitable energy levels ranging from about 8 millijoules to about 15 millijoules.

Laser source 102 also desirably emits pulses of laser beam 112 with sufficient frequencies to form trenches of encoded markings 50 along successive portions of the precursor of filament 44 while maintaining a suitable line speed for filament 44. Examples of suitable pulse frequencies for laser beam 112 range from about 500 hertz to about 1,500 hertz.

Encoder mask 104 is a mask configured to selectively form encoded marks 50 in filament 44 with laser beam 112 based on an encoding scheme. Examples of suitable encoder masks for encoder mask 104 include fixed and rotary-disk dielectric masks, such as chrome-on-fluoride masks (e.g., glass and quartz-based masks), which may contain coded patterns. For example, a rotary disk mask may contain radially coded patterns, where the timing of the pulse of laser beam 112 may select which encoded pattern is illuminated for imprinting onto filament 44.

Beam splitter 106 is configured to split laser beam 112 into separate laser beams (referred to as laser beams 112a, 112b, and 112c) for forming encoded patterns 50a, 50b, and 50c in filament 44. Reflectors 108 are reflective surfaces (e.g., dielectric mirrors) configured to reflect laser beams 112a and 112c back toward filament 44. Slot apertures 110 are spaced around filament 44 and are configured to limit the radial dimensions of encoded patterns 50a, 50b, and 50c.

During operation, the precursor of filament 44 may be fed through slot apertures 110, as shown. The information to be written to the precursor may then be encoded by a computer system (not shown) in signal communication with system 100. Based on the encoding scheme used, the computer system may direct laser source 102 pulse laser beam 112 toward encoder mask 104. The encoded pattern in encoder mask 104 may vary the patterns of laser beam 112 that pass through encoder mask 104 to beam splitter 106. Beam splitter 106 splits the portion of laser beam 112 that passed through encoder mask 104 into laser beams 112a, 112b, and 112c. Laser beams 112a, 112b, and 112c may then be directed to exterior surface 48 of the precursor of filament 44 to desirably form trenches in the precursor based on the laser beam pattern.

For example, an energy pulse of about 12 millijoules may form a trench by removing about 1.2 square millimeters (about 1,900 square mils) of a polymer (e.g., ABS) to depth of about 2.5 micrometers (about 0.1 mils). If laser beam 112 is used to form trenches that are about 0.2 millimeters (about 8 mils) wide (e.g., width 56) and about 2.5 millimeters (about 100 mils) long (e.g., length 54) with a pulse frequency of about 1,000 hertz, encoded markings 50 may be formed in the precursor at a line speed greater than about 2.5 meters/second (about 100 inches/second). As such, system 100 may be used in a continuous process with the extrusion and formation of the precursor of filament 44. The marking process may continue as successive portions of the precursor pass through system 100, thereby forming successive trenches of encoded markings 50 along length 46. The resulting filament 44 may then subjected to one or more additional steps of method 86 (e.g., steps 94, 96, and 98), as discussed above.

While marking system 100 is described above as a suitable technique for forming trenches in filaments, in alternative embodiments, marking system 100 may be configured to form cross-linked markings in the surface of filament 44. For example, the beams of ultraviolet light may cross-link the precursor material of filament 44 to vary the index of refraction at the locations of the encoded markings. This is particularly suitable in which the encoded markings function as diffraction gratings.

As discussed above, the marked consumable materials of the present disclosure allow information to be recorded in the consumable materials themselves. The encoded markings may contain a variety of information relating to the marked consumable materials and/or to the operations of the additive manufacturing systems (e.g., system 10). Additionally, the sensor assemblies (e.g., sensor assemblies 24 and 26) are configured to read the encoded markings from successive portions of the marked consumable materials as the marked consumable materials are fed to the additive manufacturing systems. This allows the additive manufacturing systems to use the information in the encoded markings for a variety of different purposes, such as for building 3D models and/or support structures.

As also discussed above, sensor assemblies 24 and 26 (shown in FIG. 1) may be retained partially or fully within supply sources 20 and 22 (shown in FIG. 1), respectively. For example, in one embodiment, sensor assembly 24 may include a first subassembly retained within system 10 at bay 20a, and a second subassembly retained within supply source 20. In this embodiment, the first and second subassemblies may engage with each other when supply source 20 is loaded to bay 20a of system 10. Sensor assembly 26 may also include the same arrangement for bay 22a and supply source 22.

FIGS. 7-12 illustrate sensor assembly 200 in use with spooled container 202, where sensor assembly 200 is an example of a suitable optical sensor assembly for use in system 10 (e.g., as sensor assembly 24 and/or sensor assembly 26, shown in FIG. 1). As shown in FIG. 2, spooled container 202 is a supply source containing filament 204, where filament 204 is a marked filament. Examples of suitable marked filaments for filament 204 include those discussed above (e.g., filaments 44 and 58).

Examples of suitable sources for spooled container 202 include those discussed above for supply sources 20 and 22 (shown in FIG. 1), such as those disclosed in Swanson et al., U.S. Pat. No. 6,923,634; Comb et al., U.S. Pat. No. 7,122,246; Taatjes et al, U.S. Patent Application Publication Nos. 2010/0096485 and 2010/0096489; and Swanson, U.S. Pat. No. 8,403,658 and International Publication No. WO2009/088995. In the shown embodiment, filament 204 may be wound around spool 206, which correspondingly may be retained in container housing 208. This arrangement allows filament 204 to be unwound from spool 206 while spool 206 rotates around hub 210 within container housing 208, as represented by arrows 212. Filament 204 may then pass through sensor assembly 200 and exit spooled container 202 to a pathway of system 10 (e.g., pathways 36 and 40), as represented by arrow 214.

Sensor assembly 200 includes subassemblies 216 and 218, which, in the shown embodiment, are separate components that may engage with each other during a build operation. Subassembly 216 is retained within system 10, outside of spooled container 202, and contains the sensor electronics (not shown in FIG. 7) for reading the encoded markings of filament 204. Subassembly 218 is retained at least partially within container housing 208 of spooled container 202, and is the portion that filament 204 passes through prior to exiting spooled container 202. In the shown embodiment, subassembly 218 is fully retained within container housing 208. As discussed below, when spooled container 202 is loaded into a bay of system 10 (e.g., bays 20a and 22a), subassembly 216 may engage with subassembly 218 to read encoded markings of filament 204 as successive portions of filament 204 pass through subassembly 218.

Figure 8:
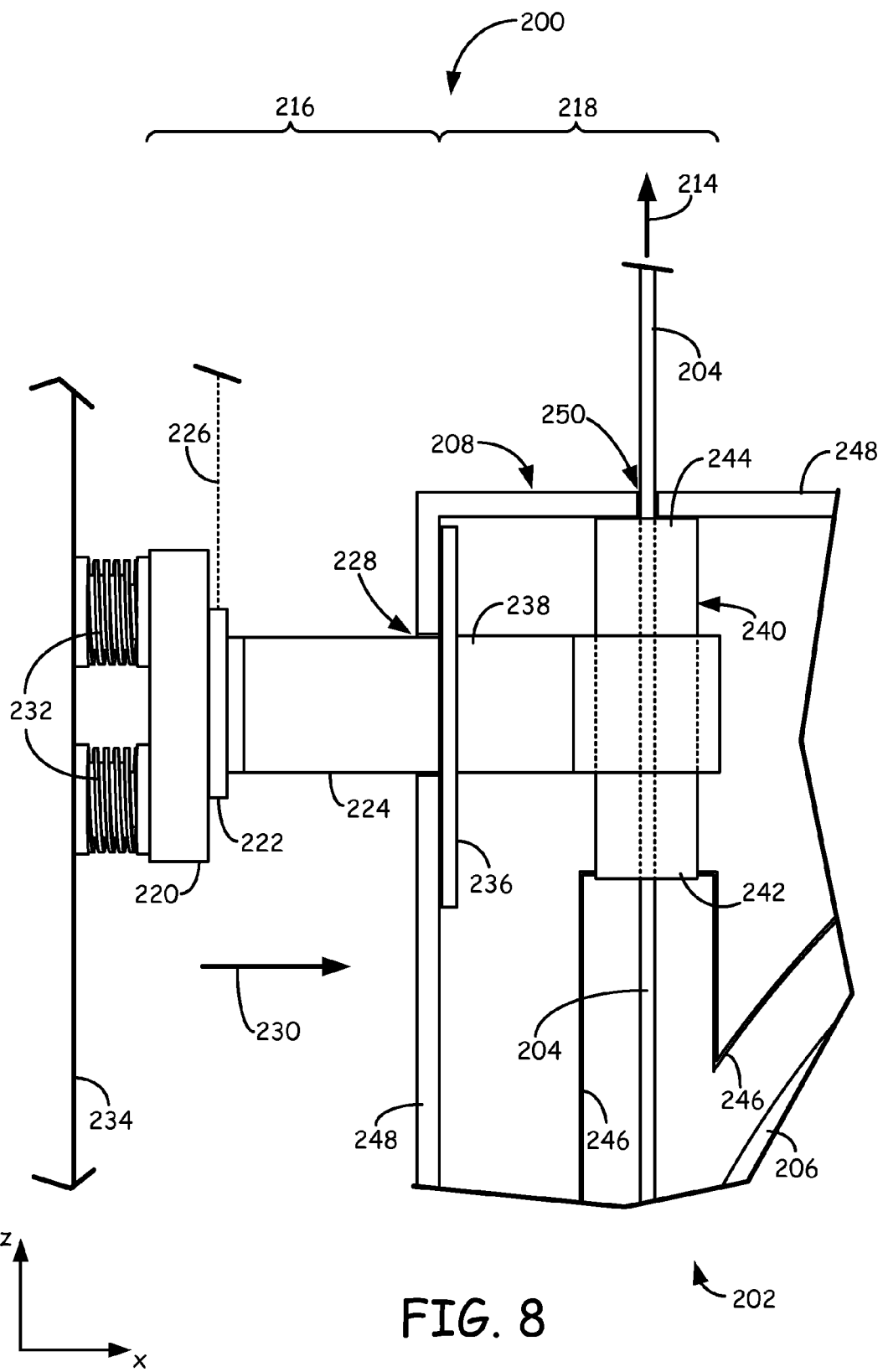
FIG. 8 is an expanded view of the sensor assembly shown in FIG. 7.

As shown in FIG. 8, subassembly 216 includes base block 220, circuit board 222, and waveguides 224. Base block 220 is a structural mount for retaining circuit board 222. In alterative embodiments, base block 220 may be omitted and circuit board 222 may be directly mounted within system 10. Circuit board 222 is a control circuit for subassembly 216 and is configured to optically read the encoded markings of filament 204 as filament 204 passes through subassembly 218 within spooled container 202. Circuit board 222 also desirably communicates with controller 32 over a communication line (e.g., communication line 226), as discussed above for communication lines 38 and 42 (shown in FIG. 1).

Waveguides 224 are a pair of waveguides (a single waveguide 224 is shown in FIG. 8), which may be fabricated as an integral unit from a transparent or translucent plastic or glass material. Waveguides 224 are configured to route light from one or more light sources (not shown in FIG. 8) mounted on circuit board 222 to subassembly 218, as discussed below. Waveguides 224 are also configured to extend into an opening within container housing 208 (referred to as opening 228) to engage subassembly 218.

As further shown in FIG. 8, subassembly 216 is biased in the direction of arrow 230 toward subassembly 218 by biasing members 232. Biasing members 232 are one or more devices configured to bias subassembly 216 toward subassembly 218 when spooled container 202 is loaded to system 10. In the shown embodiment, biasing members 232 are loaded springs located between base block 220 and the sidewall of the bay in which supply source 202 is loaded (referred to as sidewall 234). In alternative embodiments, subassembly 216 may be mounted and biased from any suitable location within system 10.

System 10 may also include one or more latching mechanisms (not shown) for retaining subassembly 216 in a retracted state against sidewall 234. In these embodiments, subassembly 216 may remain in the retracted state while spooled container 202 is being loaded or unloaded from the bay of system 10. When spooled container 202 is loaded to the bay, the latching mechanism may be released, thereby allowing subassembly 216 to engage subassembly 218.

Subassembly 218 includes window 236, waveguides 238, and filament guide 240, which may be fabricated as an integral unit from a transparent or translucent plastic or glass material. Window 236 may be secured to container housing 208 at opening 228, which allows waveguides 224 of subassembly 216 to rest against window 236 at opening 228 due to the bias in the direction of arrow 230. Waveguides 238 are a pair of waveguides (a single waveguide 238 is shown in FIG. 8) configured to route light from waveguide 224 to filament guide 240. As discussed below, filament guide 240 includes a channel for filament 204 to pass through while being fed from spooled container 202 to system 10. The biasing of waveguides 224 against window 236 also allows the focal length of sensor assembly 200 to be repeatably fixed. This arrangement allows the light routed through waveguides 224 to also be routed through waveguides 238 to filament guide 240, thereby providing a darkfield illumination for filament 204.

As discussed below, the trench edges of the encoded markings of filament 204 scatter the light of the darkfield illumination in patterns based on the encoded markings. The scattered light may be optically detected at subassembly 216, thereby allowing the information retained in the encoded markings to be read based on the patterns of the scattered light. Subassembly 216 may then transmit signals relating to the information to controller 32 over communication line 226.

In one embodiment, subassembly 218 may form a moisture barrier with container housing 208, allowing the interior of container housing 208 to retain a low moisture content. As shown, filament guide 240 includes inlet end 242 and outlet end 244. Inlet end 242 desirably forms a first moisture barrier with the interior walls of container housing 208, which define an interior region in which spool 206 may be retained (referred to as interior walls 246).

In some embodiments, spooled container 202 may include one or more liners in addition to, or as an alternative to interior walls 246. Examples of suitable liners include those disclosed in Swanson, U.S. Pat. No. 8,403,658 and International Publication No. WO2009/088995 . In these embodiments, the liner may partially or fully encase spool 206 and may be secured around inlet end 242 of filament guide 240 to maintain a moisture barrier within container housing 208.

Correspondingly, outlet end 244 desirably forms a second moisture barrier with the exterior walls of container housing 208 (referred to as exterior walls 248) at the exit orifice of container housing 208 (referred to as exit orifice 250). The pathway of system 10 to extrusion head 18 (e.g., pathways 36 and 40, not shown in FIG. 8) may also form a moisture barrier at exit orifice 250 to maintain the low moisture environment between spooled container 202 and extrusion head 18.

The moisture barriers formed between container housing 208 and filament guide 240 of subassembly 218 allow the interior region of spooled container 202 to be maintained at a low humidity level to reduce the absorption of water into filament 204. Spooled container 202 may also include desiccant packs (not shown) within the interior region to maintain a dry environment. These implementations may allow filament 204 to maintain a low moisture content (e.g., less than about 700 parts-per-million by weight) during storage and use.

Figure 9:
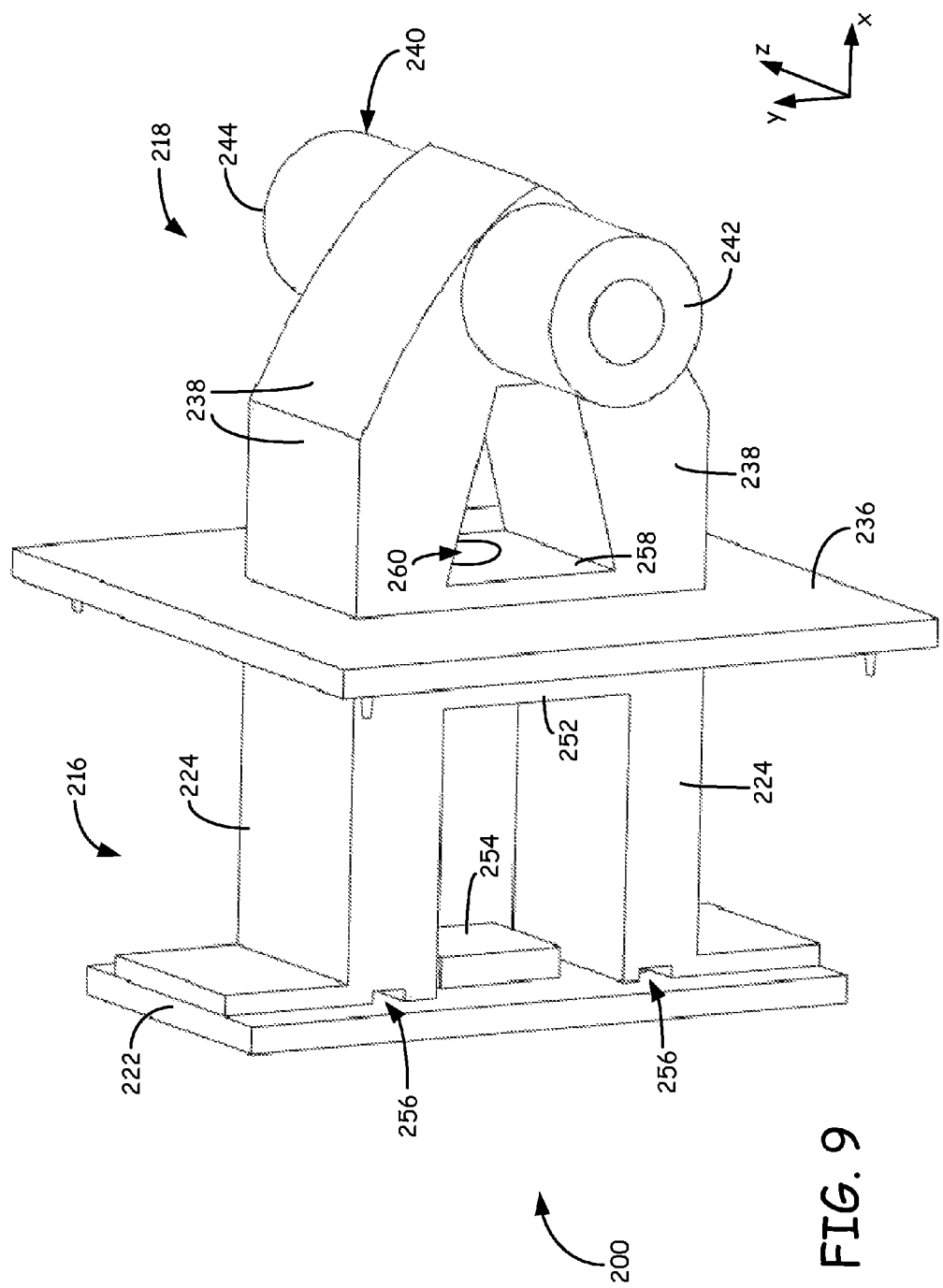
FIG. 9 is a bottom perspective view of the sensor assembly.

FIG. 9 is a bottom perspective view of sensor assembly 200, where spooled container 202 and base block 220 are omitted for ease of discussion. As shown, waveguides 224 are a first pair of waveguides that are integrally connected at bridge 252. As further shown, subassembly 216 also includes optical sensor 254, which may be secured to circuit board 222, as shown. Optical sensor 254 is a sensor configured to detect light scattered from the encoded markings of filament 204. Examples of suitable units for optical sensor 254 include one or more imaging devices, such as a complementary metal-oxide-semiconductor (CMOS) camera.

Optical sensor 254 desirably exhibits imaging capabilities to detect the scattered light patterns from the encoded markings of filament 204. Suitable imaging capabilities may vary depending on the light intensity of the darkfield illumination, the encoding scheme used, and the dimensions of the encoded markings. For example, an marking pattern of multiple marks having a length of about 2.5 millimeters may be imaged with a 2:1 magnification onto a 640×480 pixel array. Examples of suitable commercially available CMOS cameras and corresponding image processors for circuit board 222 and optical sensor 254 include those from Aptina Imaging Corporation, Grand Cayman, Ky.; and those from Toshiba Corporation, Minato, Tokyo, Japan.

As discussed below, subassembly 216 also includes a plurality of light sources (not shown in FIG. 9) mounted on circuit board 222 at indentations in waveguides 224 adjacent to circuit board 222 (referred to as indentations 256). In alternative embodiments, the light sources may be mounted at any suitable location within system 10.

Waveguides 238 are a second pair of waveguides that are integrally connected at bridge 258, where bridge 258 includes opening 260. Opening 260 provides an access location for the light reflected from filament 204 (including the light scattered from the encoded markings of filament 204) to transmit through to reach optical sensor 254. As discussed below, one or more lenses may also be located between optical sensor 254 and opening 260 for increasing or otherwise modifying the focus and magnification of the transmitted light.

As shown, when subassembly 216 engages subassembly 218, waveguides 224 substantially align with waveguides 238 along the x-axis. This allows the light routed through waveguides 224 to pass through window 236 to waveguides 238. Waveguides 238 also route the received light, and the opposing end of waveguides 238 converge toward each other around filament guide 240. This causes the routed light to reflect at least once prior reaching filament 204 to provide a darkfield illumination, as discussed below.

Figure 10:
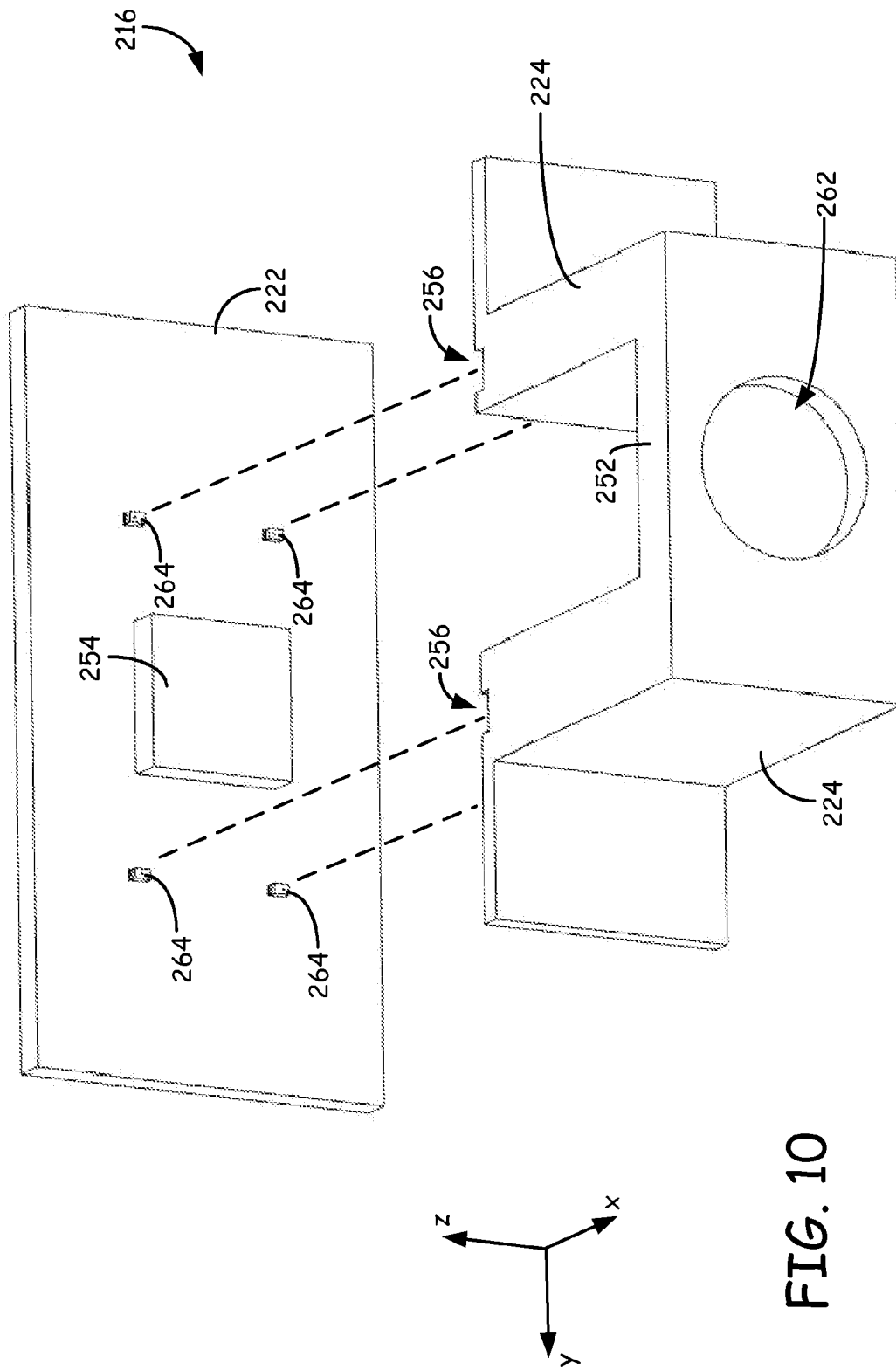
FIG. 10 is an exploded perspective view of the first subassembly of the sensor assembly.

FIG. 10 is an exploded perspective view of subassembly 216. As shown, bridge 252 of waveguides 224 includes opening 262, which desirably aligns with opening 260 (shown in FIG. 9) when subassembly 216 engages subassembly 218. As discussed above, one or both of openings 260 and 262 may retain one or more lenses for increasing or otherwise modifying the focus and magnification of the transmitted light.

As further shown in FIG. 10, light sources 264 are mounted to circuit board 222 and desirably align with indentations 256 of waveguides 224. Light sources 264 may be any suitable type of light source to provide a darkfield illumination for filament 204, such as light emitting diodes (LEDs). Additionally, while shown as two pairs of LEDs, subassembly 216 may include a variety of different numbers of light sources for providing a darkfield illumination for filament 204. In one embodiment, light sources 264 may include multiple color LEDs, such as red, green, and blue LEDs, which may be selectively used to illuminate filament 204.

Figure 11:
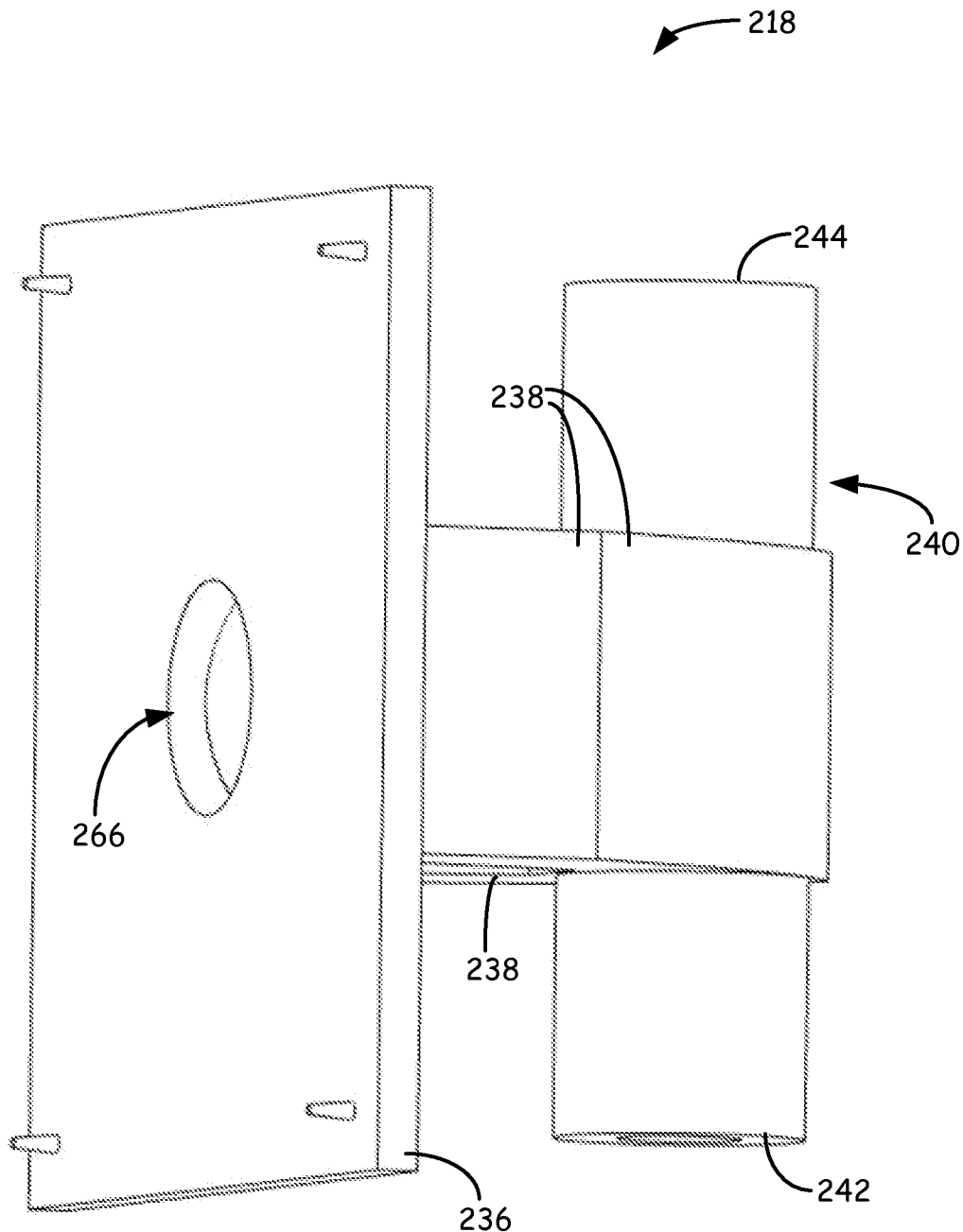
FIG. 11 is a perspective view of the second subassembly of the sensor assembly.

FIG. 11 is a perspective view of subassembly 218. As shown, window 236 of subassembly 218 also includes opening 266, which is aligned with opening 260 (shown in FIG. 9), and desirably aligns with opening 262 (shown in FIG. 10) when subassembly 216 engages subassembly 218. Openings 266 may also retain one or more lenses for increasing or otherwise modifying the focus and magnification of the transmitted light.

Figure 12:
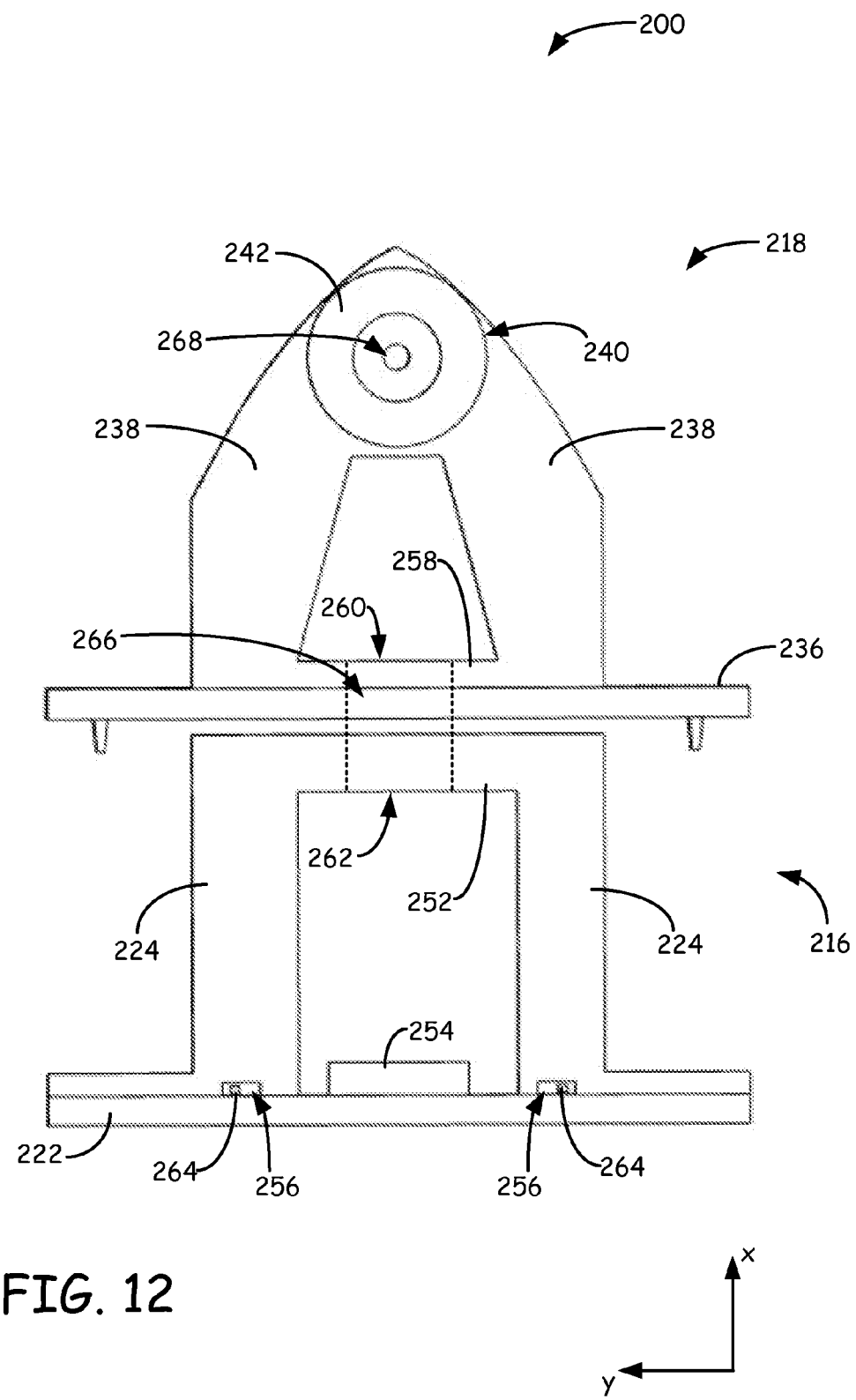
FIG. 12 is a bottom view of the sensor assembly, illustrating an engagement and operation of the first and second subassemblies.

FIG. 12 is a bottom view of sensor assembly 200, where subassembly 216 is engaged with subassembly 218. During operation, filament 204 may be fed through the channel of filament guide 240 (referred to as channel 268). Channel 268 desirably has dimensions that allow filament 204 to pass through filament guide 240 without undue friction while also desirably confining filament 204 to the object plane of optical sensor 254 such that the grazing angle input light scatters from the encoded markings of filament 204.

In embodiments in which filament 204 is a marked cylindrical filament (e.g., filament 44), suitable average inner diameters for channel 268 range from about 1.0 millimeter (about 0.04 inches) to about 3.8 millimeters (about 0.15 inches), and with particularly suitable average diameters ranging from about 1.3 millimeters (about 0.05 inches) to about 2.5 millimeters (about 0.1 inches).

In embodiments in which filament 204 is a marked non-cylindrical filament (e.g., filament 58), channel 268 may include a cross section that substantially matches the geometry of the marked non-cylindrical filament. For example, in embodiments in which the marked non-cylindrical filament has a rectangular cross section (e.g., filament 58), channel 268 desirably has a rectangular cross section with a width-to-thickness aspect ratio that substantially matches the aspect ratio of the filament. In these embodiments, suitable average widths for channel 268 range from about 1.3 millimeters (about 0.05 inches) to about 12.7 millimeters (about 0.50 inches), with particularly suitable average widths ranging from about 3.8 millimeters (about 0.15 inches) to about 10.2 millimeters (about 0.40 inches). Suitable average thicknesses for channel 268 range from about 0.25 millimeters (about 0.01 inches) to about 2.5 millimeters (about 0.1 inches), with particularly suitable average thicknesses ranging from about 0.51 millimeters (about 0.02 inches) to about 1.8 millimeters (about 0.07 inches).

The encoding scheme used desirably allows the encoded markings to be read by sensor assembly 200 without substantially affecting the drive rate of filament 204 to extrusion head 18. The drive rate of filament 204 to extrusion head 18 may vary depending the extrusion parameters in extrusion head 18 and the dimensions of filament 204. Examples of suitable drive rates range from about 2.5 millimeters/second (about 100 mils/second) to about 7.6 millimeters/second (about 300 mils/second).

As filament 204 passes through channel 268, light is emitted from light sources 264, which are routed through waveguides 224 and 238 toward filament guide 240. The converging orientations of waveguides 238 desirably cause the routed light to reflect at least once prior reaching filament 204 to provide a darkfield illumination. In particular, the light desirably reflects at least once before grazing the exterior surface of filament 204 within filament guide 240. When particular rays of the light reach the trench edges of the encoded markings of filament 204, the trench edges cause these particular rays to scatter. Accordingly, the scattering of the light follows the pattern of the encoded markings.

A portion of the reflected and scattered light may then transmit through openings 266, 260, and 262 (and through any lenses retained therein) toward optical sensor 254. Optical sensor 254 may image the received light, which, which may then be processed by circuit board 222 and/or controller 32 (via communication line 226) to decode the information from the image patterns based on the encoding scheme used. Controller 32 may then use the received information to assist in the operation to build 3D model 28 and/or support structure 30, as discussed above.

Figure 13:
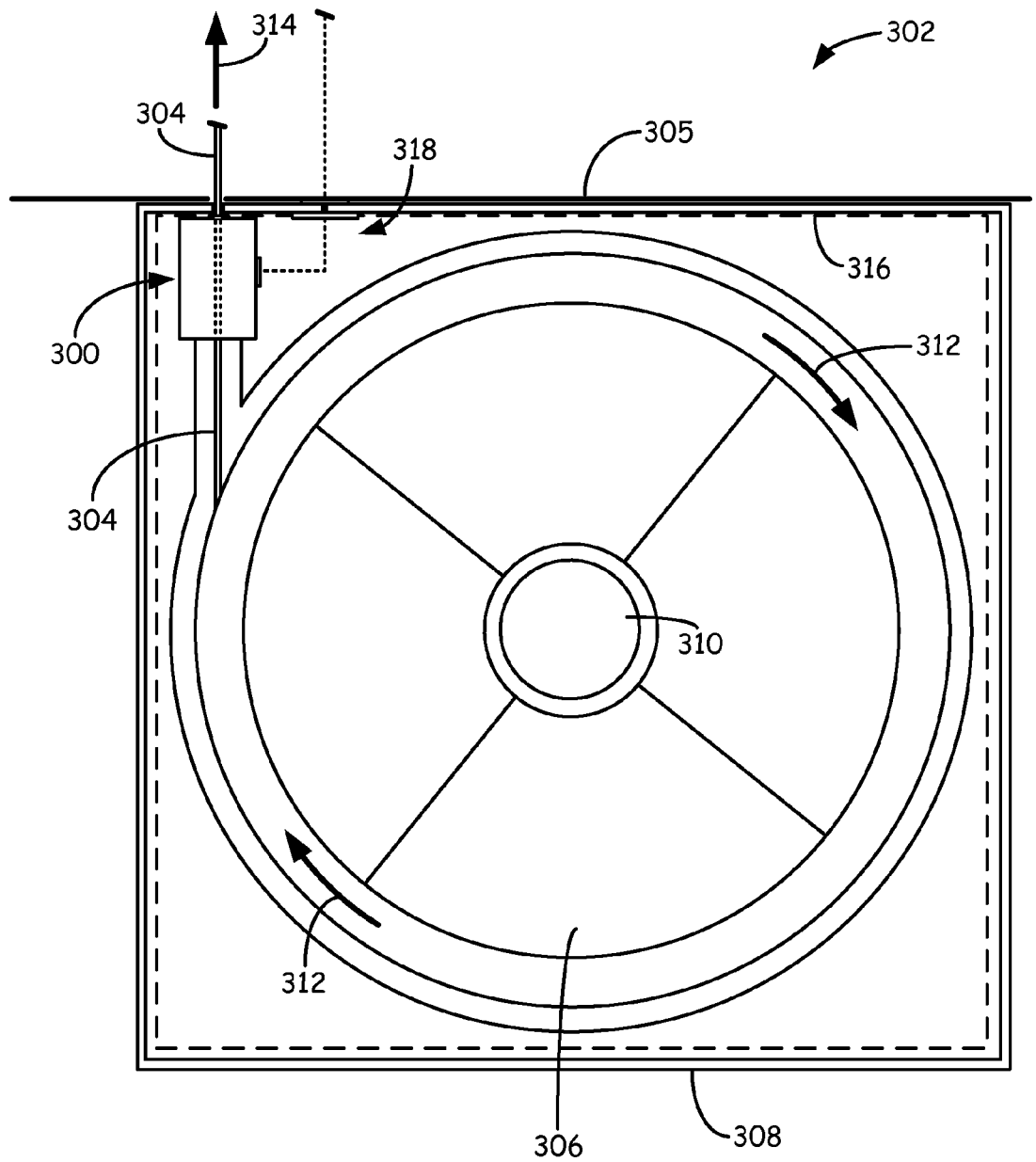
FIG. 13 is a schematic illustration of a sensor assembly of a second embodiment of the present disclosure in use with a spooled container.

In another embodiment, the sensor assemblies may be retained fully within supply sources 20 and 22, respectively. For example, FIG. 13 illustrates sensor assembly 300 in use with spooled container 302, where sensor assembly 300 is an example of a suitable sensor assembly for use in system 10 (e.g., as sensor assembly 24 and/or sensor assembly 26, shown in FIG. 1). As shown, spooled container 302 is a supply source containing filament 304, where filament 304 is a marked filament. Examples of suitable marked filaments for filament 304 include those discussed above (e.g., filaments 44 and 58). In the shown example, spooled container is mounted in a bay of system 10 (e.g., bay 20a), which includes front wall 305.

Examples of suitable sources for spooled container 302 include those discussed above for supply sources 20 and 22 (shown in FIG. 1), such as those disclosed in Swanson et al., U.S. Pat. No. 6,923,634; Comb et al., U.S. Pat. No. 7,122,246; Taatjes et al, U.S. Patent Application Publication Nos. 2010/0096485 and 2010/0096489; and Swanson, U.S. Pat. No. 8,403,658 and International Publication No. WO2009/088995. In the shown embodiment, filament 304 may be wound around spool 306, which correspondingly may be retained in container housing 308. This arrangement allows filament 304 to be unwound from spool 306 while spool 306 rotates around hub 310 within container housing 308, as represented by arrows 312. Filament 304 may then pass through sensor assembly 300 and exit spooled container 302 to a pathway of system 10 (e.g., pathways 36 and 40), as represented by arrow 314.

In the shown embodiment, spooled container 302 also includes liner 316, which includes one or more films configured to provide a moisture barrier within container housing 308. Examples of suitable liners for liner 316 include those disclosed in Swanson, U.S. Pat. No. 8,403,658 and International Publication No. WO2009/088995.

As shown, sensor assembly 300 is fully retained within housing 308, and within liner 316. While sensor assembly 300 is illustrated in FIG. 13 as being located in a particular location within housing 308 and liner 316 (i.e., in an upper-left corner in the view shown in FIG. 13), sensor assembly 300 may alternatively be disposed in other locations within housing 308 and liner 316 such that filament 304 may pass through (or adjacent to) sensor assembly 300 prior to exiting liner 316 and/or housing 308.

Sensor assembly 300 may receive electrical power from and/or communicate with system 10 via signal lines 318 or other suitable power and/or signal communication techniques. For example, signal lines 318 may be arranged in an engagement manner as disclosed in one or more of Swanson et al., U.S. Pat. No. 6,923,634; Comb et al., U.S. Pat. No. 7,122,246; Taatjes et al, U.S. Patent Application Publication Nos. 2010/0096485 and 2010/0096489; and Swanson, U.S. Pat. No. 8,403,658 and International Publication No. WO2009/088995. In the shown embodiment, a portion of signal lines 318 desirably extends through liner 316 in a sealable manner that maintains the moisture barrier.

During use, filament 304 passes through sensor assembly 300 prior to exiting liner 316 and housing 308. As such, sensor assembly 300 may read the encoded markings of filament 304 and transmit signals relating to the read markings to system 10. Sensor assembly 300 may read the encoded markings of filament 304 using a variety of different techniques, which may vary depending on the particular marking techniques used to form the encoded markings along filament 304.

Figure 14:
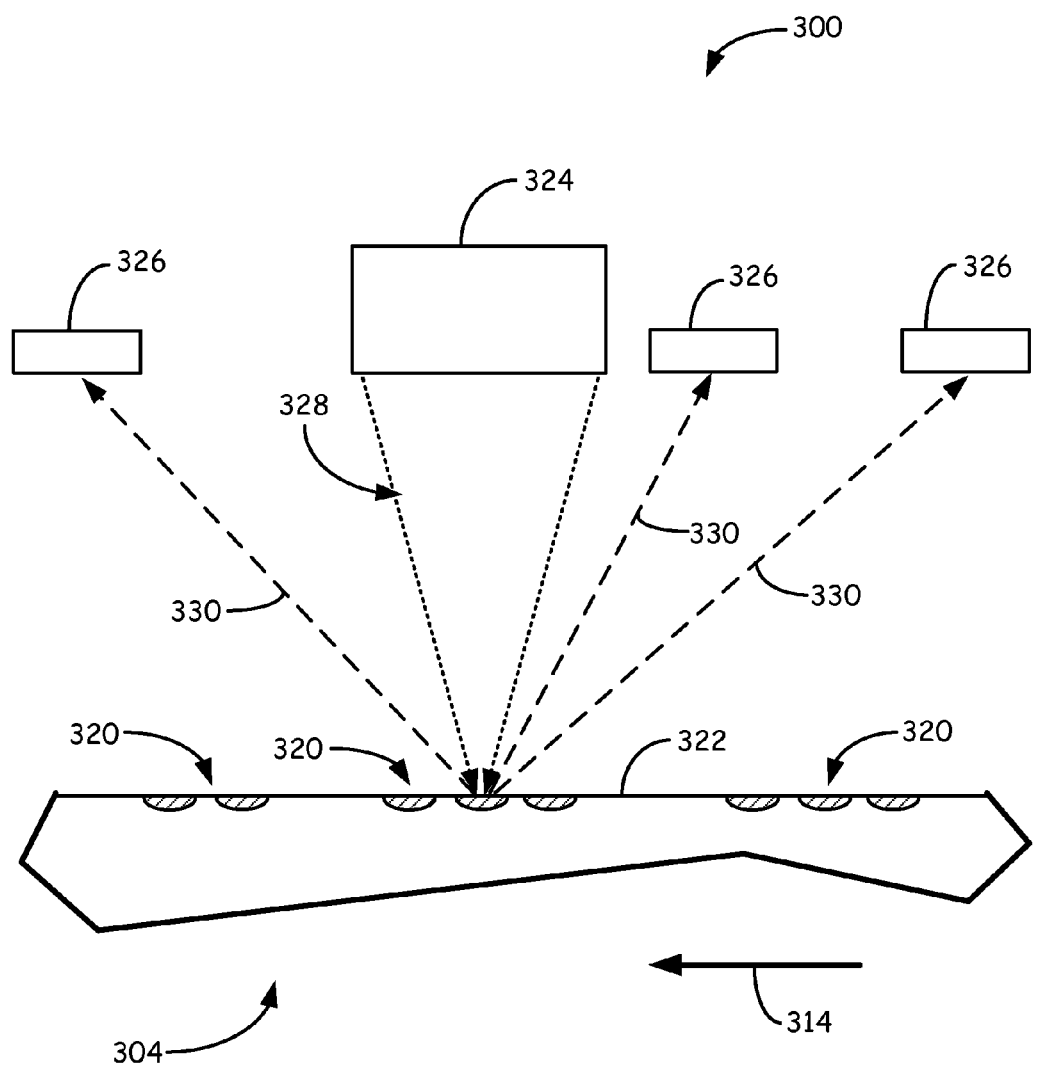
FIG. 14 is an expanded schematic illustration of an example of the second embodied sensor assembly in use with a marked consumable material, where the shown sensor assembly is configured to detect far-field diffraction patterns.

FIG. 14 is a schematic illustration of a suitable embodiment of sensor assembly 300, which is configured to read the encoded markings based on far-field diffraction patterns. As shown, in this embodiment, filament 304 includes encoded markings 320 formed on surface 322, where the pattern of encoded markings 320 function as diffraction gratings having different indices of refractions from the remaining portions of surface 322. Encoded markings 320 may be formed on or in surface 322 using one or more of the techniques discussed above. In one embodiment, the degree of cross linking of the precursor material may be locally modified by ultraviolet light to varying the index of refraction at the locations of encoded markings 320.

As further shown, sensor assembly 300 includes light emitter 324 and optical detectors 326. In alternative embodiments, sensor assembly 300 may include multiple light emitters and/or a different number of optical detectors 326. In the shown embodiment, optical detectors 326 are desirably positioned such that diffracted beams of light from encoded markings 320 are directed to optical detectors 326. The directions of the diffracted beams of light from encoded markings 320 may correspondingly be predetermined by the encoding pattern(s) of encoded markings 320.

During operation, while successive segments of filament 304 pass through sensor assembly 300 in the direction of arrow 314, light emitter 324 generates light beam 328 toward filament 304. Encoded markings 320 are configured to diffract all or a portion of the incident light beam 328 into separate diffracted beams 330. Diffracted beams 330 may be separately detected by optical detectors 326, thereby generating electrical signals indicative of the information encoded in encoded markings 320. The information may then be transmitted to controller 32 of system 10 (shown in FIG. 1) over electrical connection lines 318 (shown in FIG. 13) and communication line 36 or 40 (shown in FIG. 1). Controller 32 may then use the received information to assist in the operation to build 3D model 28 and/or support structure 30, as discussed above.

Figure 15:
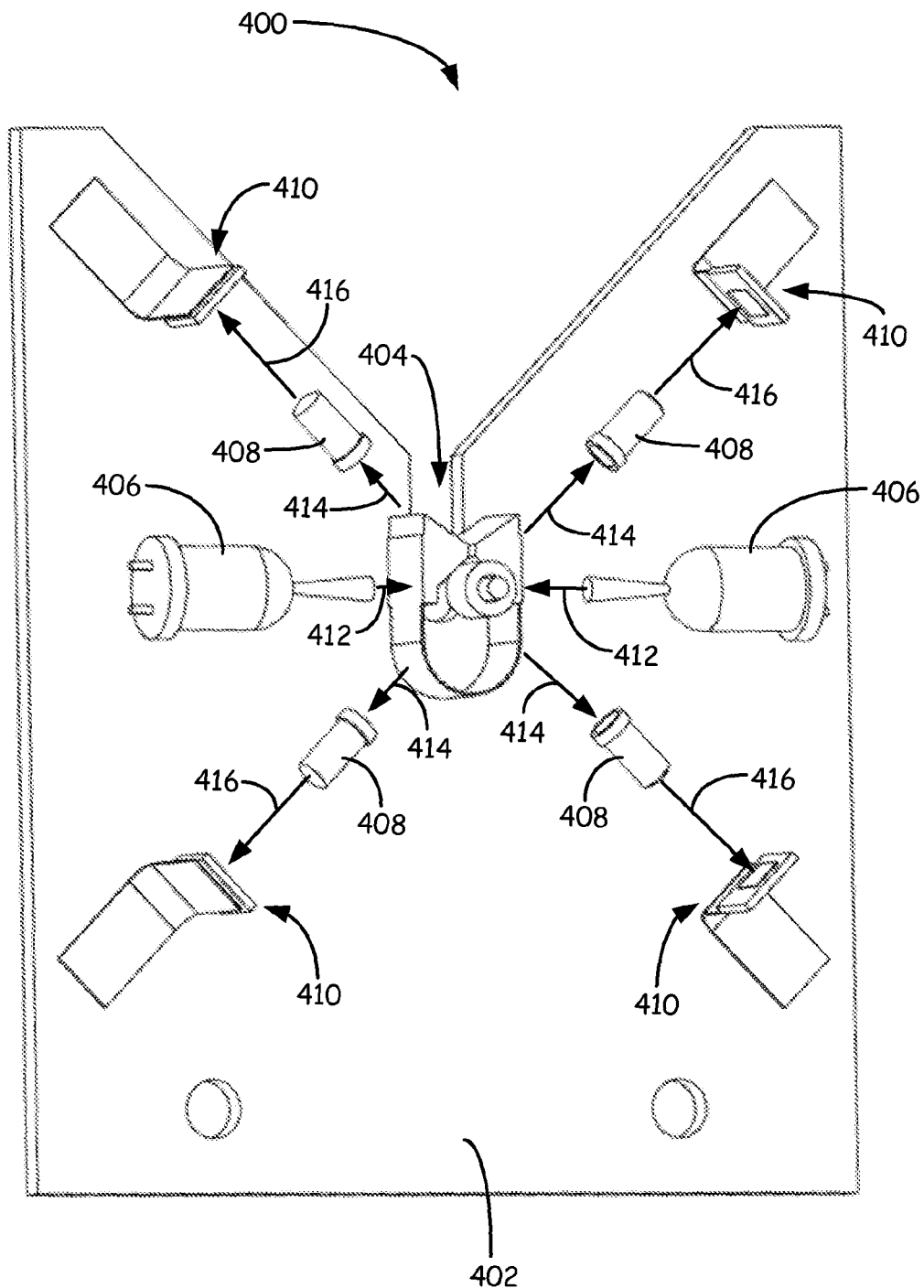
FIG. 15 is an perspective view of a sensor assembly of a third embodiment of the present disclosure.

FIG. 15 illustrates sensor assembly 400, which is an example of a suitable sensor assembly for use in system 10 (e.g., as sensor assembly 24 and/or sensor assembly 26, as shown in FIG. 2) at a location downstream from supply source 20 or supply source 22 (shown in FIG. 2). In this embodiment, sensor assembly 400 includes circuit board 402, optical assembly 404, light emitters 406, lenses 408, and optical detectors 410, where optical assembly 404, light emitters 406, lenses 408, and optical detectors 410 are secured to circuit board 402. Sensor assembly 400 may also include a housing (not shown) to protect and function as a light shield for the interior components, such as optical assembly 404, light emitters 406, lenses 408, and optical detectors 410.

Circuit board 402 is a printed circuit board operably connected to controller 32 of system 10 (shown in FIGS. 1 and 2) for relaying information and electrical power between sensor assembly 400 and controller 32. Optical assembly 404 is a component through which a marked consumable material (e.g., filament) of the present disclosure may pass through when being fed from supply source 20 or 22 to extrusion head 18, as discussed above for sensor assemblies 24 and 26 in FIG. 2.

Optical assembly 404 is desirably transparent or translucent to allow light from light emitters 406 to pass through to the marked consumable material. Light emitters are configured to emit light to optical assembly 404 (e.g., ultraviolet light), as indicated by arrows 412. The received light rays may reflect or otherwise emit from the marked consumable material based on the patterns of the encoded markings. For example, in embodiment in which the light rays are ultraviolet light rays and the encoded markings are derived from ultraviolet-activated materials (e.g., fluorescent materials), the ultraviolet-activated materials may emit activated light rays (e.g., fluorescent light) upon receiving the ultraviolet light rays.

Portions of the reflected or emitted light rays from the marked consumable material are directed to lenses 408, as indicated by arrows 414. Lenses 408 accordingly may redirect the received light rays toward optical detectors 410, as indicated by arrows 416. Optical detectors 410 may then generate electrical signals indicative of the information encoded in the encoded markings, which may then be transmitted to controller 32 communication line 36 or 40 (shown in FIG. 2). Controller 32 may then use the received information to assist in the operation to build 3D model 28 and/or support structure 30, as discussed above.

The use of four sets of lenses 408 and optical detectors 410 is suitable for detecting encoded markings located at any location on the exterior surface of the marked consumable material. In alternative embodiments, such as those in which the marked consumable material include multiple rows of the encoded markings (e.g., encoded markings separated by about 60 degree arcs around a cylindrical filament), sensor assembly 400 may include fewer sets of lenses 408 and optical detectors 410.

As discussed above, the marked consumable materials of the present disclosure allow information to be recorded in the consumable materials themselves. The encoded markings may contain a variety of information relating to the marked consumable materials and/or to the operations of the direct digital or additive manufacturing systems (e.g., system 10). Additionally, the sensor assemblies (e.g., sensor assemblies 24, 26, 200, 300, and 400) are configured to read the encoded markings from successive portions of the marked consumable materials as the marked consumable materials are fed to the additive manufacturing systems. This allows the additive manufacturing systems to use the information in the encoded markings for a variety of different purposes, such as for building 3D models and/or support structures.

Although the present disclosure has been described with reference to preferred embodiments, workers skilled in the art will recognize that changes may be made in form and detail without departing from the spirit and scope of the disclosure.

The invention claimed is:

1. A method for building a three-dimensional model with an additive manufacturing system, the method comprising:
   providing a marked filament to the additive manufacturing system, the marked filament comprising volume-increment markings that are offset from each other along a longitudinal length of the marked filament by increment lengths that vary to define segments of the filament having volumes that are substantially the same;
   feeding the marked filament to an extrusion head liquefier retained by the additive manufacturing system;
   reading the volume-increment markings of the fed marked filament with an optical sensor assembly retained by the additive manufacturing system;
   transmitting signals relating to the read volume-increment markings from the optical sensor assembly to a control component of the additive manufacturing system;

melting the marked filament to at least an extrudable state in the extrusion head liquefier;

depositing the melted material from the extrusion head liquefier to form the three-dimensional model in a layer-by-layer manner; and adjusting a feed rate of the marked filament to the extrusion head liquefier based in part on the transmitted signals relating to the volume-increment markings.

2. The method of claim 1, wherein the volume-increment markings extend substantially along the entire longitudinal length of the marked filament.

3. The method of claim 1, wherein the marked filament compositionally comprises a thermoplastic material, and wherein the volume-increment markings comprise an ultraviolet-activated material.

4. The method of claim 1, wherein the marked filament comprises a cylindrical filament having a substantially cylindrical geometry with an average diameter ranging from about 0.8 millimeters to about 2.5 millimeters.

5. The method of claim 1, wherein the marked filament comprises a ribbon filament having a cross section with a width and thickness, wherein the width of the cross section ranges from about 1.0 millimeter to about 10.2 millimeters, and wherein the thickness of the cross section ranges from about 0.08 millimeters to about 1.5 millimeters.

6. The method of claim 1, wherein the volume-increment markings comprise sub-marks denoting an encoding scheme for additional information, and wherein the method further comprises adjusting at least one property of the additive manufacturing system based on the additional information.

7. The method of claim 6, wherein the additional information in the sub-markings comprises local filament cross-sections, material type, material composition, manufacturing information for the marked filament, product code, material origin information, or combinations thereof.

8. A method for building a three-dimensional model with an additive manufacturing system, the method comprising:

providing a marked filament to the additive manufacturing system, the marked filament comprising volume-increment markings that are offset from each other along a longitudinal length of the marked filament to define a plurality of segments of the filament, wherein the plurality of segments of the filament comprise:

a first segment having a first increment length and a first volume; and a second segment having a second increment length and a second volume, wherein the first increment length is different from the second increment length, and the first volume is substantially the same as the second volume;

feeding the marked filament to an extrusion head liquefier retained by the additive manufacturing system;

reading the volume-increment markings of the fed marked filament with an optical sensor assembly retained by the additive manufacturing system;

transmitting signals relating to the read volume-increment markings from the optical sensor assembly to a control component of the additive manufacturing system;

melting the marked filament to at least an extrudable state in the extrusion head liquefier;

depositing the melted material from the extrusion head liquefier to form the three-dimensional model in a layer-by-layer manner; and adjusting a feed rate of the marked filament to the extrusion head liquefier based in part on the transmitted signals relating to the volume-increment markings.

9. The method of claim 8, wherein the volume-increment markings extend substantially along the entire longitudinal length of the marked filament.

10. The method of claim 8, wherein the marked filament compositionally comprises a thermoplastic material, and wherein the volume-increment markings comprise an ultraviolet-activated material.

11. The method of claim 8, wherein the marked filament comprises a cylindrical filament having a substantially cylindrical geometry with an average diameter ranging from about 0.8 millimeters to about 2.5 millimeters.

12. The method of claim 8, wherein the marked filament comprises a ribbon filament having a cross section with a width and thickness, wherein the width of the cross section ranges from about 1.0 millimeter to about 10.2 millimeters, and wherein the thickness of the cross section ranges from about 0.08 millimeters to about 1.5 millimeters.

13. The method of claim 8, wherein the volume-increment markings comprise sub-marks denoting an encoding scheme for additional information, and wherein the method further comprises adjusting at least one property of the additive manufacturing system based on the additional information.

14. A method for building a three-dimensional model with an additive manufacturing system, the method comprising:

providing a supply source of a marked filament to the additive manufacturing system, the marked filament comprising volume-increment markings that are offset from each other along a longitudinal length of the marked filament by increment lengths that vary to define segments of the filament having volumes that are substantially the same;

feeding the marked filament from the supply source to an extrusion head liquefier retained by the additive manufacturing system;

reading the volume-increment markings of the fed marked filament with an optical sensor assembly located between the supply source and the extrusion head liquefier;

transmitting signals relating to the read volume-increment markings from the optical sensor assembly to a control component of the additive manufacturing system;

extruding a material of the marked filament from the extrusion head liquefier to form the three-dimensional model in a layer-by-layer manner; and adjusting a feed rate of the marked filament to the extrusion head liquefier based in part on the transmitted signals relating to the volume-increment markings.

15. The method of claim 14, wherein the volume-increment markings extend substantially along the entire longitudinal length of the marked filament.

16. The method of claim 14, wherein the material of the marked filament comprises a thermoplastic material, and wherein the volume-increment markings comprise an ultraviolet-activated material.

17. The method of claim 14, wherein the marked filament comprises a cylindrical filament or a ribbon filament.

18. The method of claim 14, wherein the supply source comprises a spooled container.

19. The method of claim 14, wherein the volume-increment markings comprise sub-marks denoting an encoding scheme for additional information, and wherein the method further comprises adjusting at least one property of the additive manufacturing system based on the additional information.

20. The method of claim 14, wherein the optical sensor assembly is retained by the additive manufacturing system at a location that is separate from the supply source and from the extrusion head liquefier, and wherein feeding the marked filament from the supply source to the extrusion head liquefier comprises moving the marked filament through the optical sensor assembly.

* * * * *